(12) United States Patent
Jimenez et al.

(10) Patent No.: US 8,523,944 B2
(45) Date of Patent: Sep. 3, 2013

(54) METHODS AND APPARATUS FOR VERTEBRAL BODY DISTRACTION AND FUSION EMPLOYING FLEXURE MEMBERS

(75) Inventors: Omar F. Jimenez, Gering, NE (US); Nicholas Ransom Powley, St. Paul, MN (US)

(73) Assignee: SpineX Tec, LLC, Gering, NE (US)

( * ) Notice: Subject to any disclaimer, the term of this patent is extended or adjusted under 35 U.S.C. 154(b) by 671 days.

(21) Appl. No.: 12/650,994

(22) Filed: Dec. 31, 2009

(65) Prior Publication Data
US 2010/0185291 A1    Jul. 22, 2010

Related U.S. Application Data

(60) Provisional application No. 61/142,104, filed on Dec. 31, 2008, provisional application No. 61/291,203, filed on Dec. 30, 2009.

(51) Int. Cl.
*A61F 2/44* (2006.01)

(52) U.S. Cl.
USPC .................................. 623/17.15; 623/17.16

(58) Field of Classification Search
USPC .................. 623/17.11, 17.13, 17.15, 17.16
See application file for complete search history.

(56) References Cited

U.S. PATENT DOCUMENTS

| | | | |
|---|---|---|---|
| 2,106,088 A | 1/1938 | De Tar | |
| 2,231,221 A | 2/1941 | Rector | |
| 2,453,656 A | 11/1948 | Bullard | |
| 2,666,334 A | 1/1954 | Nalle | |
| 2,711,105 A | 6/1955 | Williams | |
| 2,842,976 A | 7/1958 | Young | |
| 3,386,128 A | 6/1968 | Vyvyan | |
| 3,449,971 A | 6/1969 | Posh | |
| 3,575,475 A | 4/1971 | Boerner | |
| 3,596,863 A | 8/1971 | Kaspareck | |
| 3,597,938 A | 8/1971 | Hellen | |
| 3,700,289 A | 10/1972 | Bilinski | |
| 3,700,290 A | 10/1972 | Ensinger | |
| 3,708,925 A | 1/1973 | Ainoura | |
| 3,709,132 A | 1/1973 | Farrell | |
| 3,916,596 A | 11/1975 | Hawley | |

(Continued)

FOREIGN PATENT DOCUMENTS

| EP | 1342456 | 9/2003 |
|---|---|---|
| EP | 1881209 | 10/2008 |

(Continued)

OTHER PUBLICATIONS

International Search Report, mailed Jul. 14, 2011, Application No. PCT/US2009/069876, filed Dec. 30, 2009, 7 pages.

(Continued)

*Primary Examiner* — Andrew Yang
(74) *Attorney, Agent, or Firm* — Patterson Thuente Pedersen, P.A.

(57) ABSTRACT

Improved methods and apparatuses for vertebral body distraction and fusion in accordance with various embodiments of the present invention employ flexure members. Flexure members connect a plurality of structural members to end plates on one end and blocks on another end. Upon insertion into the disc space, a drive screw or similar mechanism can be actuated to drive expansion blocks closer together, which causes flexure members to deflect, resulting in expansion of the structural members and distraction of the end plates. The distracted device can then remain in the body and be used for vertebral body fusion.

17 Claims, 38 Drawing Sheets

(56) References Cited

U.S. PATENT DOCUMENTS

| | | |
|---|---|---|
| 3,985,000 A | 10/1976 | Hartz |
| 3,988,906 A | 11/1976 | Smith |
| 4,261,211 A | 4/1981 | Haberland |
| 4,478,109 A | 10/1984 | Kobelt |
| 4,528,864 A | 7/1985 | Craig |
| 4,559,717 A | 12/1985 | Scire |
| 4,630,495 A | 12/1986 | Smith |
| 4,691,586 A | 9/1987 | Van Leijenhorst |
| 4,694,703 A | 9/1987 | Routson |
| 4,869,552 A | 9/1989 | Tolleson |
| 5,133,108 A | 7/1992 | Esnault |
| 5,181,371 A | 1/1993 | Deworth |
| 5,196,857 A | 3/1993 | Chiappetta |
| 5,198,932 A | 3/1993 | Takamura |
| 5,374,556 A | 12/1994 | Bennett |
| 5,439,377 A | 8/1995 | Milanovich |
| 5,445,471 A | 8/1995 | Wexler |
| 5,645,599 A | 7/1997 | Samani |
| 5,664,457 A | 9/1997 | Nejati |
| 5,904,479 A | 5/1999 | Staples |
| 5,960,670 A | 10/1999 | Iverson |
| 5,980,252 A | 11/1999 | Samchukov |
| 5,988,006 A | 11/1999 | Fleytman |
| 6,045,579 A | 4/2000 | Hochshuler |
| 6,175,989 B1 | 4/2000 | Hochshuler |
| 6,056,491 A | 5/2000 | Hsu |
| 6,136,031 A | 10/2000 | Middleton |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina |
| 6,454,806 B1 | 9/2002 | Cohen |
| 6,484,608 B1 | 11/2002 | Ziavras |
| 6,517,772 B1 | 2/2003 | Woolf |
| 6,554,526 B1 | 4/2003 | Egelandsdal |
| 6,641,614 B1 | 11/2003 | Wagner |
| 6,719,796 B2 | 4/2004 | Cohen |
| 6,772,479 B2 | 8/2004 | Hinkley |
| 6,802,229 B1 | 10/2004 | Lambert |
| 6,808,537 B2 | 10/2004 | Michelson |
| 6,863,673 B2 | 3/2005 | Gerbec |
| 6,932,844 B2 | 8/2005 | Ralph |
| 6,953,477 B2 | 10/2005 | Berry |
| 7,018,415 B1 | 3/2006 | McKay |
| 7,051,610 B2 | 5/2006 | Stoianovici |
| 7,070,598 B2 | 7/2006 | Lim |
| 7,201,751 B2 | 4/2007 | Zucherman |
| 7,273,373 B2 | 9/2007 | Horiuchi |
| 7,308,747 B2 | 12/2007 | Smith |
| 7,316,381 B2 | 1/2008 | Hacker |
| 7,410,201 B1 | 8/2008 | Wilson |
| 7,425,103 B2 | 9/2008 | Perez-Sanchez |
| 7,435,032 B1 | 10/2008 | Murphey |
| 7,584,682 B2 | 9/2009 | Hsiao |
| 7,611,538 B2 | 11/2009 | Belliard |
| 7,674,296 B2 | 3/2010 | Rhoda |
| 7,682,376 B2 | 3/2010 | Trieu |
| 7,708,779 B2 | 5/2010 | Edie |
| 7,753,958 B2 | 7/2010 | Gordon |
| 7,758,645 B2 | 7/2010 | Studer |
| 7,758,648 B2 | 7/2010 | Castleman |
| 7,892,285 B2 | 2/2011 | Viker |
| 7,947,078 B2 | 5/2011 | Siegal |
| 2003/0077110 A1 | 4/2003 | Knowles |
| 2003/0233145 A1 | 12/2003 | Landry |
| 2004/0111157 A1 | 6/2004 | Ralph |
| 2004/0225364 A1 | 11/2004 | Marc et al. |
| 2005/0000228 A1 | 1/2005 | De Sousa |
| 2005/0033431 A1 | 2/2005 | Gordon |
| 2005/0095384 A1 | 5/2005 | Wittmeyer |
| 2005/0113924 A1 | 5/2005 | Buttermann |
| 2005/0175406 A1 | 8/2005 | Perez-Sanchez |
| 2006/0004447 A1 | 1/2006 | Mastrorio |
| 2006/0004455 A1* | 1/2006 | Leonard et al. ............ 623/17.15 |
| 2006/0025862 A1 | 2/2006 | Villiers et al. |
| 2006/0129244 A1 | 6/2006 | Ensign |
| 2006/0149385 A1 | 7/2006 | McKay |
| 2006/0184171 A1 | 8/2006 | Biedermann |
| 2006/0247781 A1 | 11/2006 | Francis |
| 2006/0293752 A1 | 12/2006 | Moumene |
| 2007/0049943 A1 | 3/2007 | Moskowitz |
| 2007/0083267 A1 | 4/2007 | Miz |
| 2007/0129730 A1 | 6/2007 | Woods et al. |
| 2007/0185577 A1 | 8/2007 | Malek |
| 2007/0191954 A1 | 8/2007 | Hansell |
| 2007/0191958 A1 | 8/2007 | Abdou |
| 2007/0219634 A1 | 9/2007 | Greenhalgh |
| 2007/0222100 A1* | 9/2007 | Husted et al. ............... 264/109 |
| 2007/0282449 A1 | 12/2007 | Villiers |
| 2007/0293329 A1 | 12/2007 | Glimpel |
| 2007/0293948 A1 | 12/2007 | Bagga |
| 2008/0026903 A1 | 1/2008 | Flugrad |
| 2008/0077246 A1 | 3/2008 | Fehling |
| 2008/0100179 A1 | 5/2008 | Ruggeri |
| 2008/0161920 A1 | 7/2008 | Melkent |
| 2008/0161931 A1 | 7/2008 | Perez-Cruet |
| 2008/0168855 A1 | 7/2008 | Giefer |
| 2008/0188941 A1 | 8/2008 | Grotz |
| 2008/0210039 A1 | 9/2008 | Brun |
| 2008/0221694 A1 | 9/2008 | Warnick |
| 2008/0234736 A1 | 9/2008 | Trieu |
| 2008/0281423 A1 | 11/2008 | Sheffer |
| 2008/0292392 A1 | 11/2008 | Voellmer |
| 2008/0319487 A1 | 12/2008 | Fielding |
| 2009/0012564 A1 | 1/2009 | Chirico |
| 2009/0076614 A1 | 3/2009 | Arramon |
| 2009/0164017 A1 | 6/2009 | Sommerich |
| 2009/0222100 A1 | 9/2009 | Cipoletti |
| 2010/0004688 A1 | 1/2010 | Maas |
| 2010/0082109 A1 | 4/2010 | Greenhalgh |
| 2010/0094305 A1 | 4/2010 | Chang |
| 2010/0185291 A1 | 7/2010 | Omar |
| 2010/0209184 A1 | 8/2010 | Omar |
| 2011/0093075 A1 | 4/2011 | Duplessis |
| 2011/0112644 A1 | 5/2011 | Zilberstein |

FOREIGN PATENT DOCUMENTS

| | | |
|---|---|---|
| JP | 05-81194 | 11/1993 |
| JP | 2004-301135 | 10/2004 |
| JP | 2008-208932 | 9/2008 |
| WO | WO 2004/026188 | 4/2004 |
| WO | WO 2004/109155 | 12/2004 |
| WO | WO 2005/081330 | 9/2005 |
| WO | WO 2006/094535 | 9/2006 |
| WO | WO 2006/116052 | 11/2006 |
| WO | WO 2006/125329 | 11/2006 |
| WO | WO 2007/002583 | 1/2007 |
| WO | WO 2007/028140 | 3/2007 |
| WO | WO 2007/111979 | 10/2007 |
| WO | WO 2008/137192 | 11/2008 |
| WO | WO 2009/018349 | 2/2009 |
| WO | WO 2010/078520 | 12/2009 |

OTHER PUBLICATIONS

International Search Report and Written Opinion of the International Searching Authority or the Declaration dated Sep. 27, 2010, International Application No. PCT/US2009/069876, filed Dec. 30, 2009, 12 pages.

International Search Report and Written Opinion of the International Searching Authority or the Declaration dated Nov. 29, 2010, International Application No. PCT/US2009/069958, filed Dec. 31, 2009, 9 pages.

Wenzel Spine, Inc., *VariLift®—L Expandable Interbody Fusion Device: A proven solution for stand-alone fusion*, Product Overview, 12 pages, © 2010.

Peter A. Halverson, et. al., Tension-based Multi-stable Compliant: Rolling-contact Elements, Department of Mechanical Engineering, Brigham Young University, Provo UT, USA 84602 (34 pages), 2007.

Just L. Herder, Force Directed Design of Laparoscopic Forceps, 1998, ASME Design Engineering Technical Conference (8 pages).

Alexander H. Slocum, Fundamentals of Design (2005).

Amelie Jeanneau, et. al., *A Compliant Rolling Contact Joint and its Application in a 3-DOF Planar Parallel Mechanism with Kinematic Analysis*, ASME (2004) Design Engineering Technical Conferences (9 pages).

Application and File History of U.S. Appl. No. 12/651,266, Inventors Jimenez et al., filed Dec. 31, 2009.

Application and File History of U.S. Appl. No. 12/407,608, Inventors Omar F. Jimenez, filed Mar. 19, 2009.

Application and File History of U.S. Appl. No. 12/841,465, Inventors Jimenez et al., filed Jul. 22, 2010.

Application and File History of U.S. Appl. No. 12/841,869, Inventors Jimenez et al., filed Jul. 22, 2010.

W. Kiisswetter, *A Supplementary Instrumentation for Posterior Fusion of Spine in Scoliosis*, Archives of Orthopedic Traumatic Surgery, 1980, 1 page.

Chou et al., *Efficacy of Anterior Cervical Fusion: Comparison of Titanium Cages*, polyetheretherketone (*PEEK*) *cages and autogenous bone grafts*, Journal of Clinical Neuroscience, 2008, pp. 1240-1245.

Hunter et al., *Overview of Medical Devices*, Department of Radiology, University of Arizona, Aug. 2001, pp. 89-140, vol. 30, No. 4, ISSN: 0363-0188.

Notification of Transmittal of the International Search Report and the Written Opinion of the International Searching Authority or the Declaration, Application No. PCT/US2010/042941, mailed Apr. 25, 2011.

International Search Report, Application No. PCT/US2010/042915, mailed Apr. 22, 2011.

Application No. PCT/US2009/069958, *Notification Concerning Transmittal of International Preliminary Report on Patentability*, mailed Jul. 14, 2011, 4 pages.

* cited by examiner

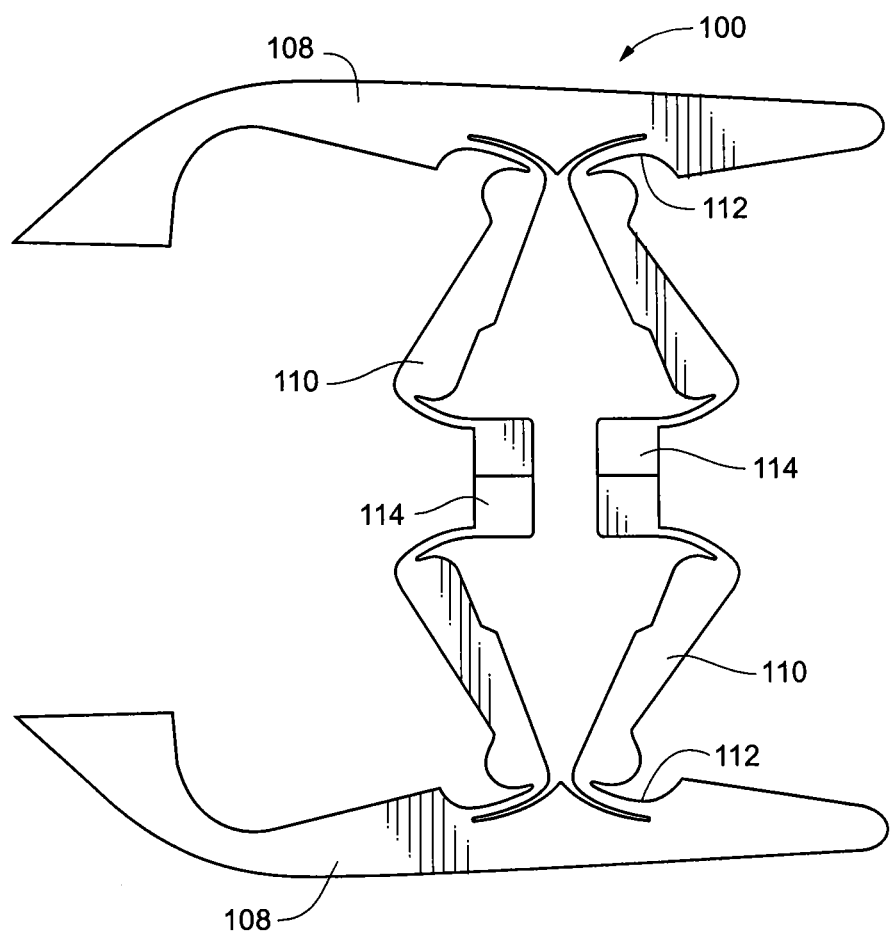

METHODS AND APPARATUS FOR VERTEBRAL BODY DISTRACTION AND FUSION EMPLOYING FLEXURE MEMBERS

PRIORITY

The present application claims the benefit of U.S. Provisional Application No. 61/142,104, filed Dec. 31, 2008 and U.S. Provisional Application No. 61/291,203, filed Dec. 30, 2009, each of which is incorporated herein in its entirety by reference.

FIELD OF THE INVENTION

The present invention relates to the distraction and fusion of vertebral bodies. More specifically, the present invention relates to devices and methods for distraction and fusion of vertebral bodies employing flexural members.

BACKGROUND OF THE INVENTION

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root to allow load sharing to enhance bone formation, and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomic challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

SUMMARY OF THE INVENTION

Improved methods and apparatuses for vertebral body distraction and fusion in accordance with various embodiments of the present invention employ flexure members. Flexure members connect a plurality of structural members to end plates on one end and blocks on another end. Upon insertion into the disc space, a drive screw or similar mechanism can be actuated to drive expansion blocks closer together, which causes flexure members to deflect, resulting in expansion of the structural members and distraction of the end plates. The distracted device can then remain in the body and be used for vertebral body fusion.

In one embodiment, a device can be used for both intervertebral body distraction and fusion. The device includes a one-piece device body comprised of a ductile material. The device body can include a pair of opposed end plates, a plurality of structural members, and flexure members attaching one end of each structural member to an end plate and the other end of each structural member to a block. The device body can include two sets of structural members, or struts, on each side or three or more struts. Drive screws, for example, can be inserted through expansion blocks and actuated to drive the expansion blocks closer together, resulting in deflection of the flexure members, which causes expansion of the struts and distraction of the end plates. The flexure members allow a one-piece device to behave similarly to a device having multiple parts and rotating pin joints.

In another embodiment, a method of intervertebral body distraction and fusion involves implantation of a distractible intervertebral body fusion device. Once the device is inserted into the disc space with an implantation tool, drive screws can be actuated to deflect flexure members on device, causing end plates to distract. After the end plates have reached a desired distraction, a bone growth stimulant can be delivered into the open area of the distracted device. The implantation tool can be withdrawn, and the device can remain in the body to aid in the fusion process and support in-vivo loads. In another embodiment, the bone growth stimulant can be added to a chamber within the device prior to implantation of the device.

In one embodiment, the flexure members are arranged so as to create a double-sided rolling flexure arrangement that enables rolling contacts of the flexure element between two rolling contact surfaces. In one embodiment, the two rolling contact surfaces are each curved. In another embodiment, the rolling contact surface closer to the strut element is straight, while the other rolling contact surface is convex as viewed from the long axis of the strut. In this way, a system having rigid bars, links or struts can form a multiple bar linkage by the use of the flexure members as described in the various embodiments as revolute joints. Advantages of these arrangements permit increases in the effective stiffness, strength, and fatigue life of the apparatus and the ability to resist buckling, while permitting a large range of motion.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 7 is a side view of an embodiment of a distractible intervertebral body fusion device according to an aspect of the present invention.

Figure 1A:
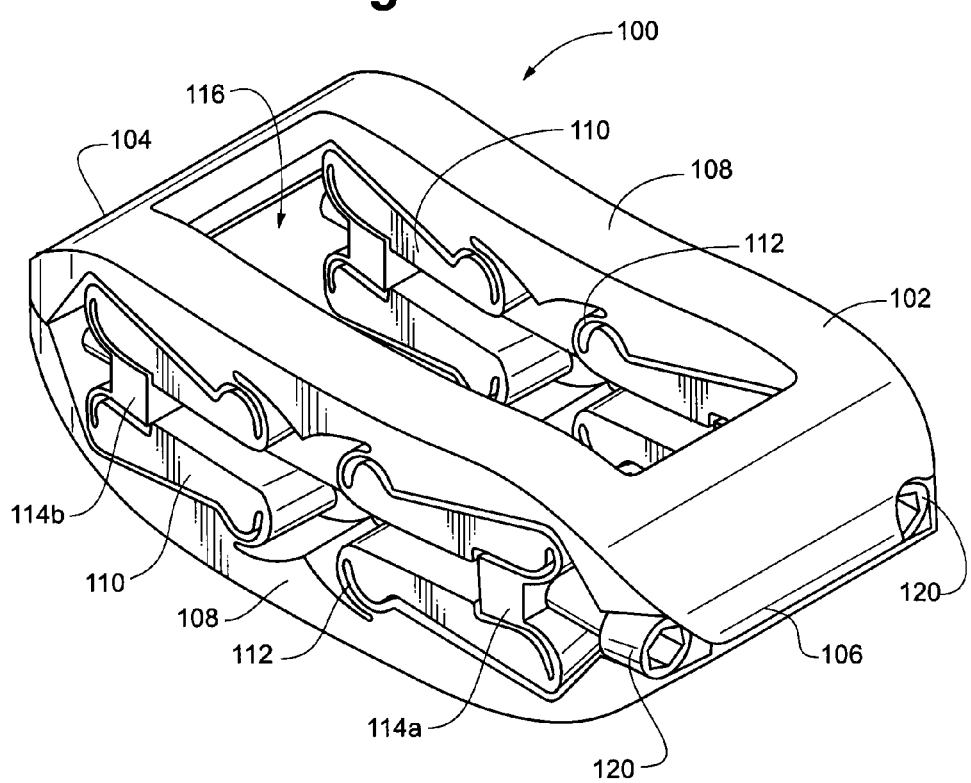
FIG. 1A is a perspective view of an embodiment of a distractible intervertebral body fusion device according to an aspect of the present invention.
Figure 1B:
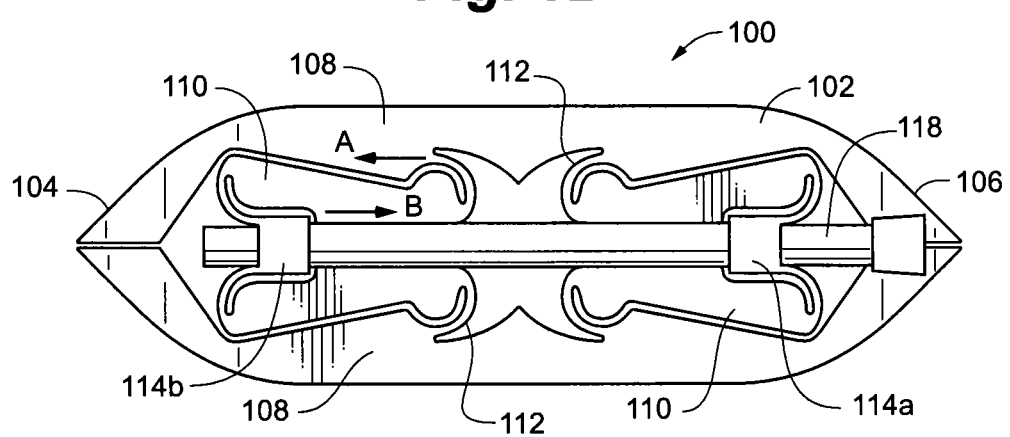
FIG. 1B is a side view of the distractible intervertebral body fusion device of FIG. 1A.
Figure 1C:
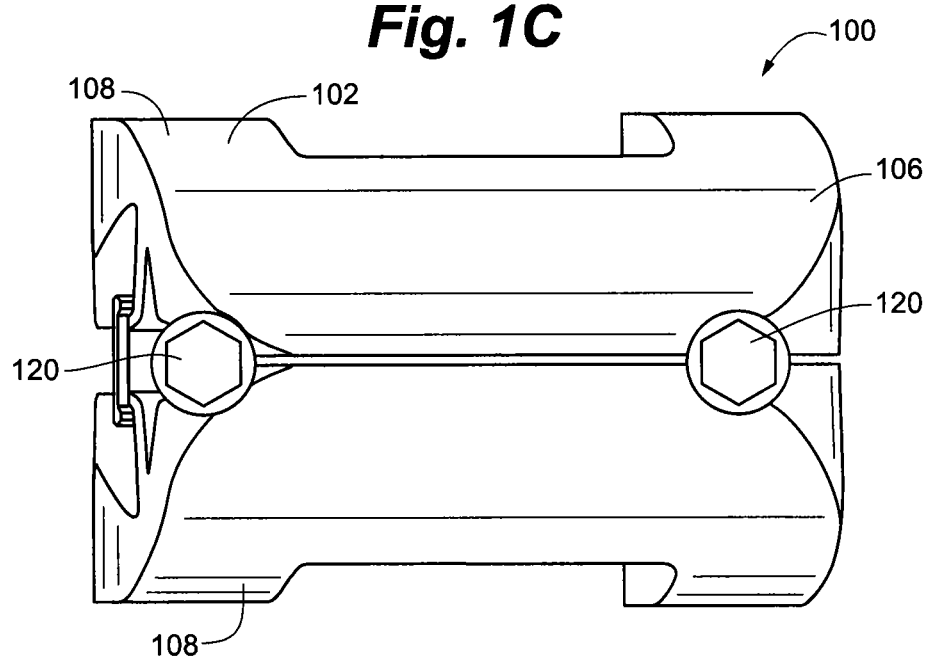
FIG. 1C is an end view of the distractible intervertebral body fusion device of FIG. 1A.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the various embodiments of the present invention.

Referring to FIGS. 1A-1C and 2A-2B there can be seen a distractible intervertebral body fusion device 100 according to an aspect of the present invention. Device 100 includes a device body 102. Device body 102 can include a nose portion 104, a rear portion 106, a pair of opposed end plates 108, structural members 110 and flexure members 112 attaching one end of the structural members 110 to end plates 108 and the other end of structural members 110 to blocks 114a, 114b.

Figure 2A:
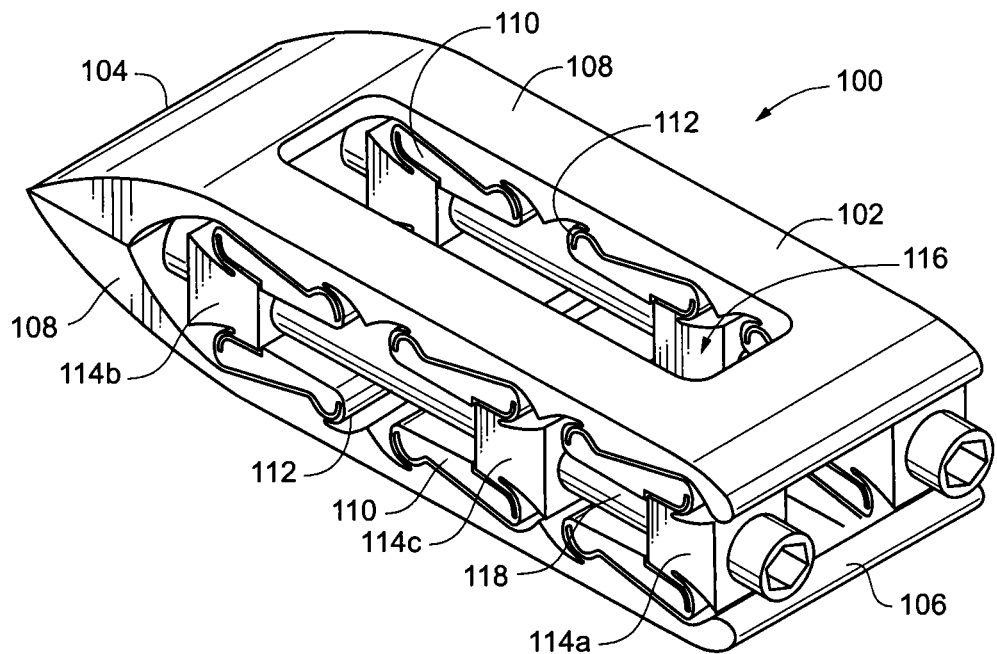
FIG. 2A is a perspective view of an embodiment of a distractible intervertebral body fusion device according to an aspect of the present invention.
Figure 2B:
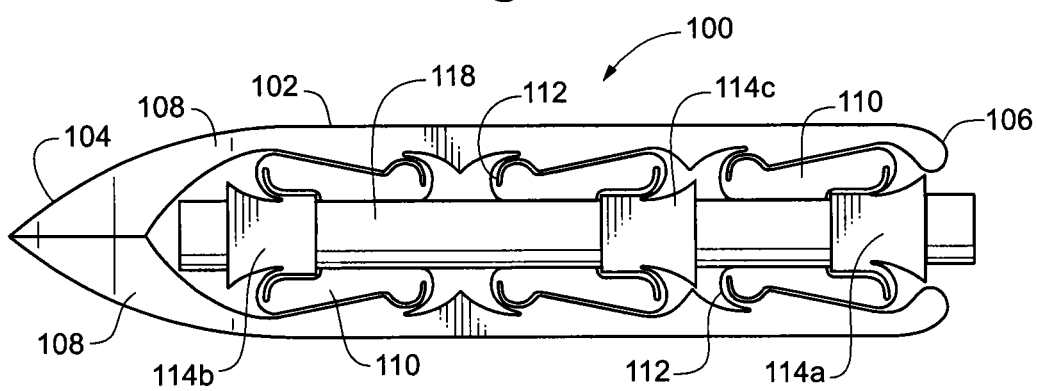
FIG. 2B is a side view of the distractible intervertebral body fusion device of FIG. 2A.
Figure 16:
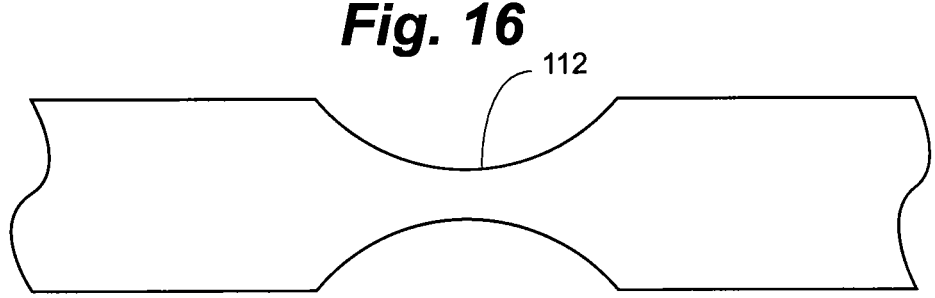
FIG. 16 is a side view of a circular flexure.
Figure 17:
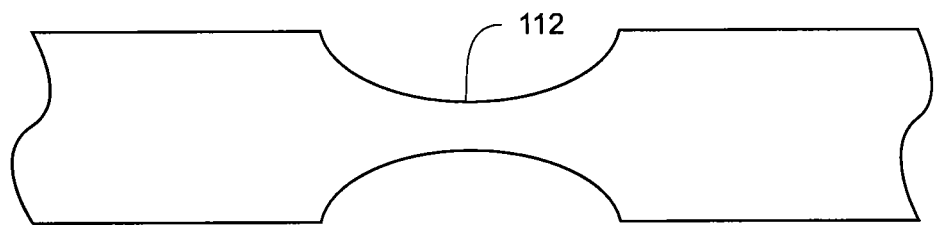
FIG. 17 is a side view of an elliptical flexure.
Figure 18:
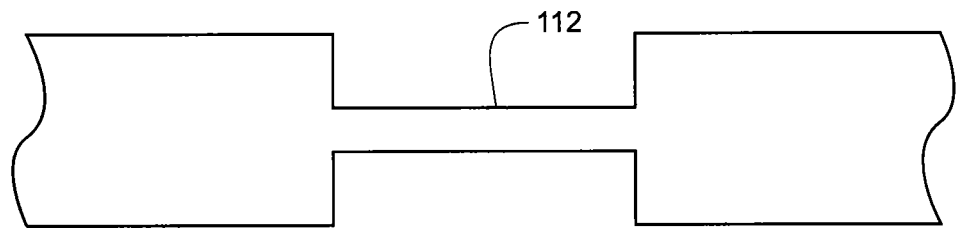
FIG. 18 is a side view of a leaf flexure.

Device body 102 can include two sets of structural members 110, or struts, on each side (FIGS. 1A-1D) or can include three, or more, sets of structural members 110 on each side (FIGS. 2A-2B). As will be discussed in more detail herein, addition of a third strut provides greater stability to the device 100. Flexure members 112 are thin strips of material that connect the structural members to the end plates 108 and expansion blocks 114. The flexure members 112 allow a one-piece device 100 to behave similarly to a device having multiple parts and a rotating pin joint. Flexure members 112 can, for example, be band flexures (FIGS. 1A-1C and 2A-2B), circular flexures (FIG. 16), elliptical flexures (FIGS. 17 and 20A-B), or leaf flexures (FIGS. 18, 19A-B, 21A-B and 22A-B).

In one embodiment, each end plate 108 includes a rectangular opening 116. Opening can be used to facilitate bone growth through the device 100. In other embodiments, opening 116 can be filled with a gel, rubber, or other complaint material that can replicate the nucleus of an interverterbral disc and supplement the strength of the flexures 112 in compressive, shear, and torsional loading conditions. Alternatively, a generally solid surface or a surface with multiple openings can be provided on each end plate 108. End plates 108 can have a rough surface or teeth to create friction with the end plates of the vertebra to prevent accidental extrusion of the device 100. In one embodiment, the device body 102, or portions of the device body 102, can be overmolded with a polymer or other material to supplement the strength of the device. For example, long carbon nanotube chains can be applied to the surface of the device so that as the device distracts the carbon nanotubes align along the surface of the flexures to add to the stability of the device.

Nose portion 104 can be tapered to facilitate the insertion of the device 100 into the disc space. Rear portion 106 can also be tapered. In one embodiment, nose portion 104 and rear portion 106 can be left open to accommodate a tapered delivery shaft that can extend all the way through the device 100.

Figure 23A:
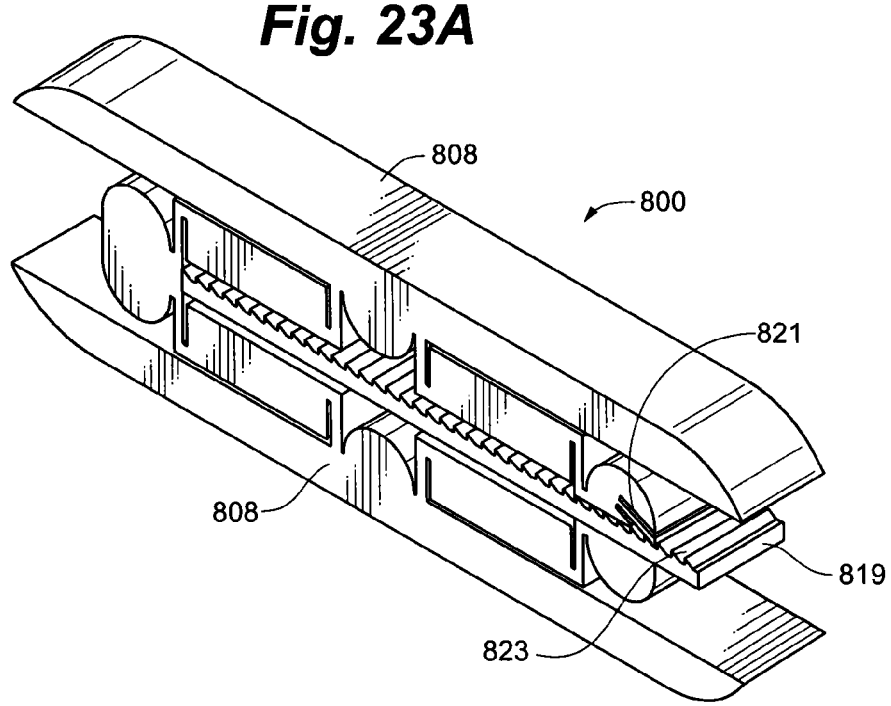
FIG. 23A is a perspective view of a distractible intervertebral body fusion device according to an aspect of the present invention.
Figure 23B:
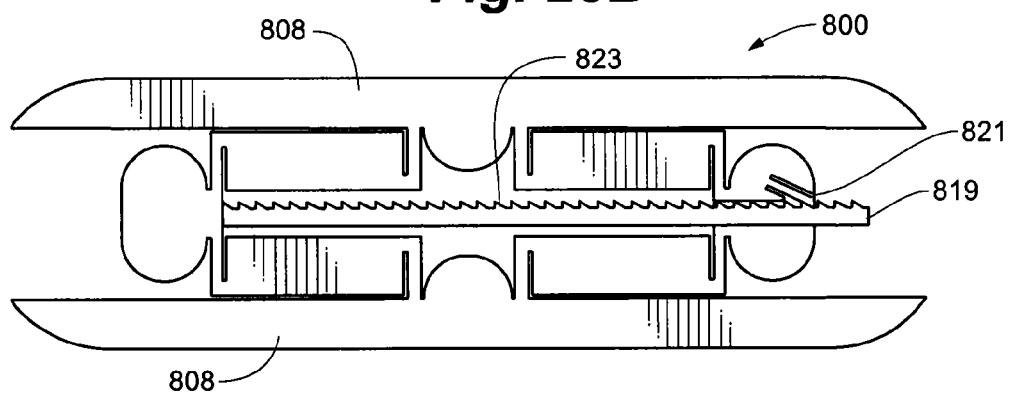
FIG. 23B is a side view of the distractible intervertebral body fusion device of FIG. 23A.

Drive screws 118 can be inserted through guide apertures 120 in rear portion 106 and through expansion blocks 114. Actuation of drive screws 118 drives blocks 114 closer together, which causes deflection of the flexure members 112, resulting in expansion of the structural members 110 and distraction of the end plates 108. In one embodiment, blocks 114b in FIGS. 1A-1C can be tapped to accommodate drive screws 118 and blocks 114a can provide a clearance fit with screws 118. When drive screws 118 are actuated, this allows blocks 114a to be pulled towards blocks 114b, causing the device 100 to distract. Similarly, blocks 114a and 114c in FIGS. 2A-2B can be tapped and blocks 114b can provide a clearance fit. In such a configuration, the opposite end from the hex of screws 118 can have a shoulder to draw block 114b towards blocks 114c and 114a. In some embodiments, mechanisms other than drive screws can be used to distract device. Such mechanisms include, for example, a pop-rivet mechanism, a sardine key and ribbon, a tourniquet and wire, a saw blade/ratchet, and shape changing materials such as a shape memory alloy or a conducting polymer actuator. In one embodiment depicted in FIGS. 23A and 23B, a zip-tie-like drive mechanism 819 can be used to distract end plates 808 of device 800. The rear block 814 can include a projection 821 for engaging the teeth 823 of the drive mechanism 819. In one embodiment, piezo-electric inch-worm motors can be used to actuate the movement of blocks 114. In another embodiment, a balloon can be inserted into device and inflated to expand the device. The balloon can remain in the device and function like the nucleus of a disc.

In various embodiments, device body 102 is shaped to be ergonomic. Device body 102 can have various shapes, such as, for example, rectangular, kidney, or football shaped. A kidney or football shaped device body 102 maximizes contact between the device and the vertebral bodies because the end plates of vertebrae tend to be slightly concave. One or both ends of the device may also be tapered in order to facilitate insertion. This minimizes the amount of force needed to initially insert the device and separate the vertebral bodies. In addition, the device may be convex along both its length and its width, or bi-convex. Device 100 can be constructed in various sizes depending on the type of vertebra and size of patient with which it is being used.

Device body 102 can also be comprised of various materials. In one embodiment, device is comprised of a ductile material. Such materials can include, for example, titanium, nitinol, and thermoplastics. In some embodiments, the material near the ends of the flexures 112 can be cold-worked to increase the stiffness of the device as it distracts. Heat treating could also be used to alleviate machining stresses and could be followed by hardening treatment to make the device stiffer. Additionally, in some embodiments the flexures can be affixed to the device in subsequent manufacturing steps in order to permit the flexures to be made from a different material or materials, or materials treated differently, than the structural members and end plates of the device. Flexures could also be laminated beams having a core of another stiff material, a soft material such as a foam, or an open core. Having a soft or open core would allow the flexures to effectively decrease in thickness as they are bent around the curved surfaces of the struts. This would decrease the amount of strain present in the flexure due to bending, allowing the device to accommodate greater functional loading.

Figure 3:
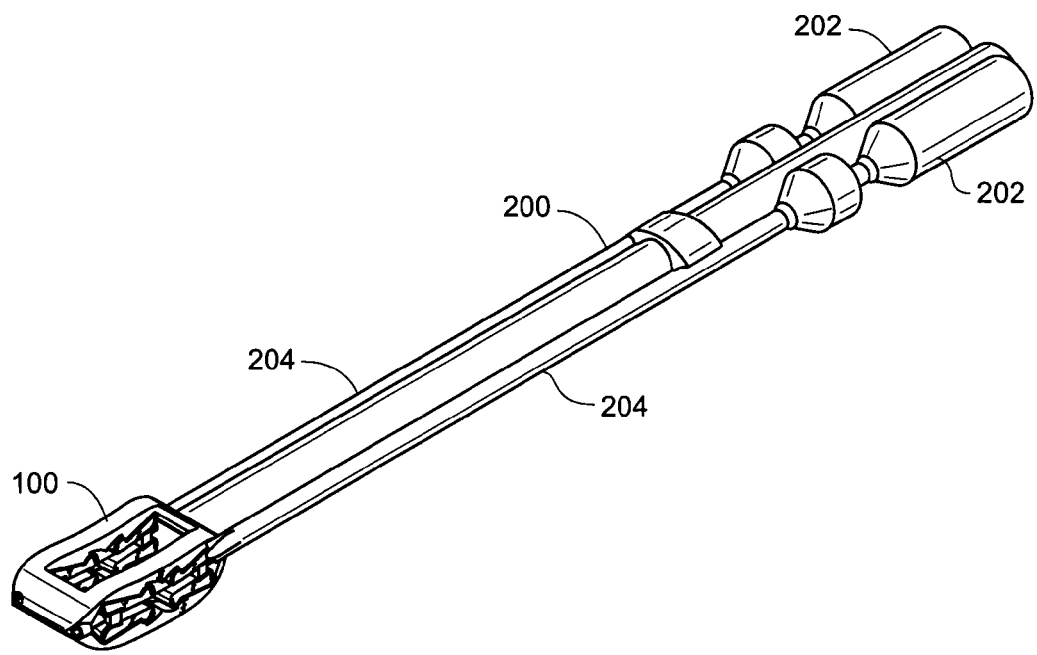
FIG. 3 is a perspective view of an embodiment of a distractible intervertebral body fusion device and an insertion tool according to an aspect of the present invention.
Figure 4:
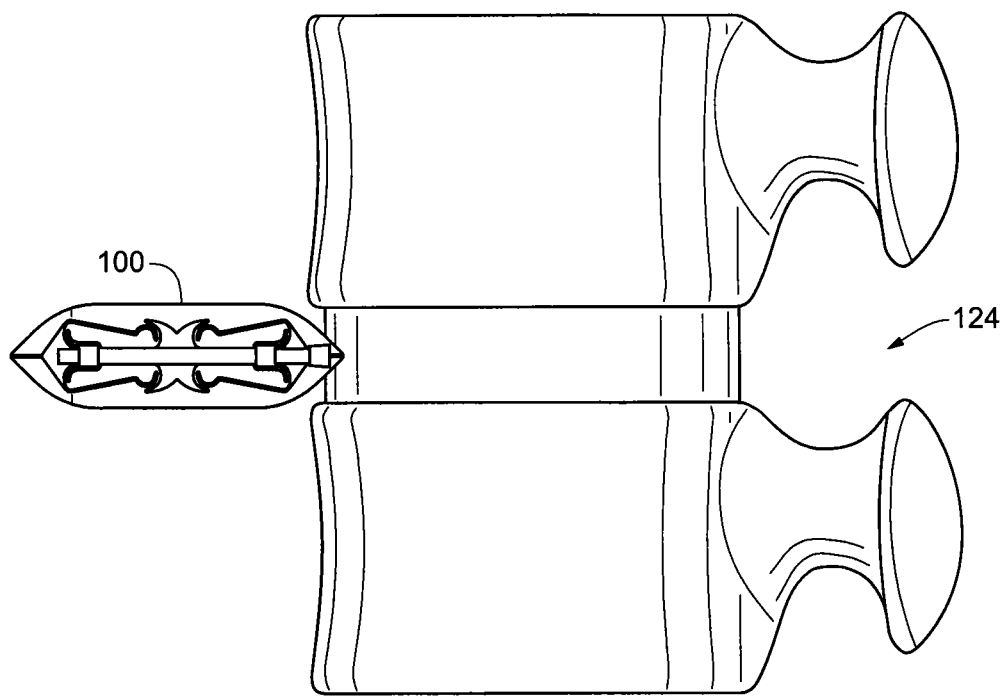
FIG. 4 is a side view of an embodiment of a distractible intervertebral body fusion device being inserted into a disc space according to an aspect of the present invention.
Figure 5:
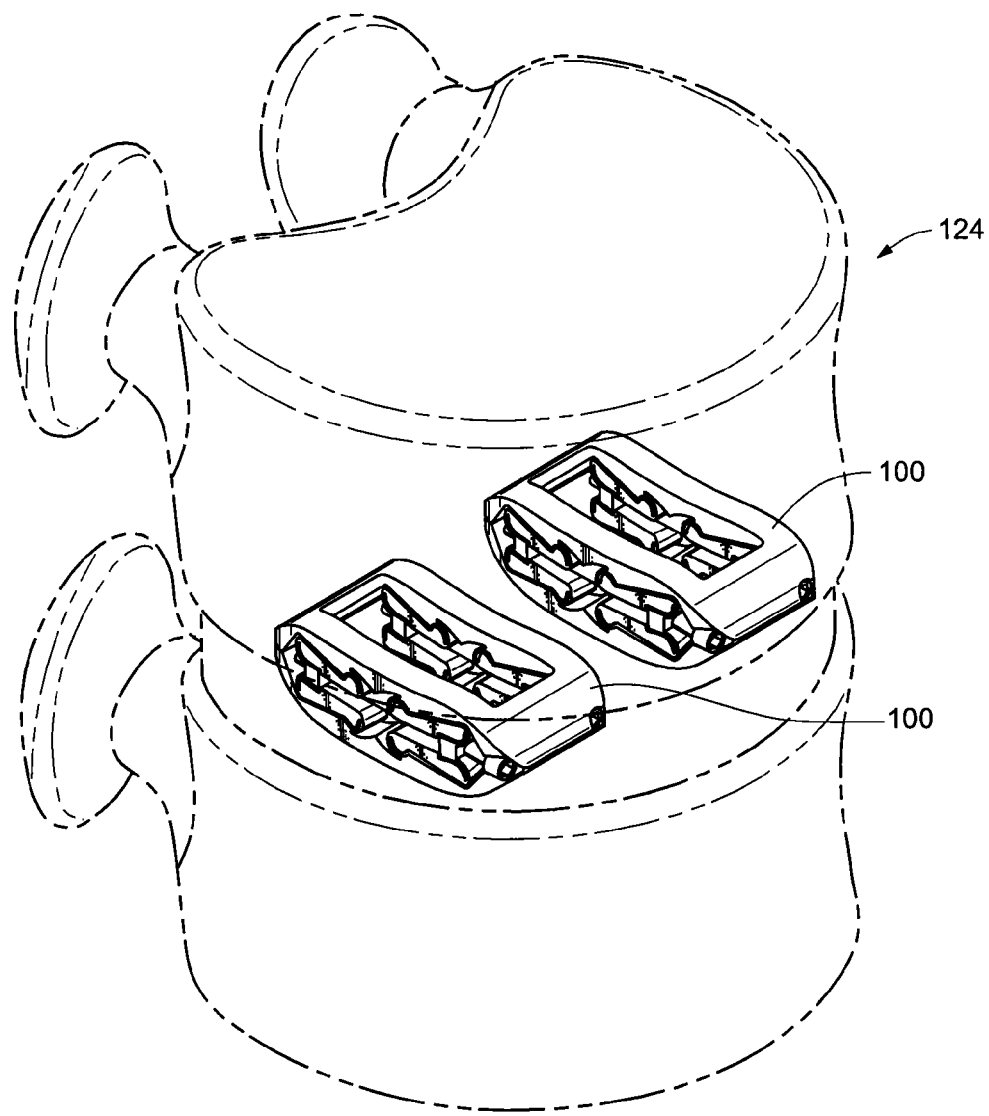
FIG. 5 is a perspective view of a pair of distractible intervertebral body fusion devices inserted into a disc space according to an aspect of the present invention.
Figure 33A:
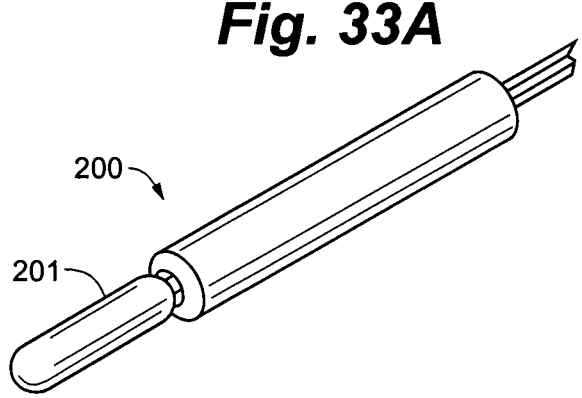
FIG. 33A is a partial perspective view of an embodiment of an insertion tool according to an aspect of the present invention.
Figure 33B:
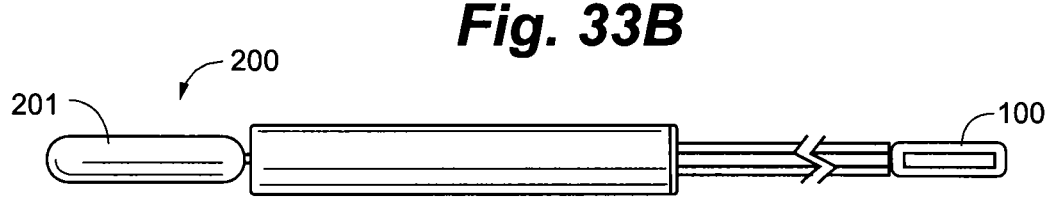
FIG. 33B is a partial top view of the insertion tool of FIG. 33A and a distractible intervertebral body fusion device according to an aspect of the present invention.
Figure 33C:
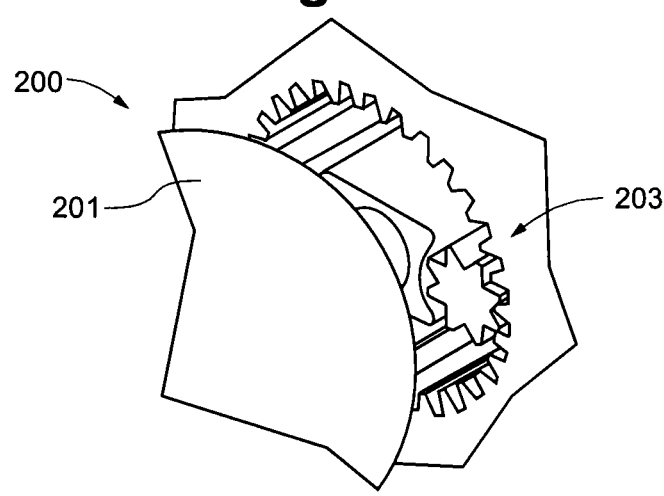
FIG. 33C is a partial perspective view of the insertion tool of FIG. 33A.

Device 100 can be placed between adjacent vertebra or vertebral bodies and used both to distract the endplates of the adjacent vertebral bodies and serve as a fusion device. An insertion tool 200 can be used to insert a device between vertebral bodies 124 as shown in FIGS. 3-5. In one embodiment, insertion tool 200 can include a pair of parallel screwdrivers or wrenches 202 temporarily affixed to the drive screws 118 with retainers 204. In one embodiment shown in FIG. 3, insertion tool 200 extends rearwardly from device 100. In another embodiment, insertion tool 200 may also extend distally from device 100. In such an embodiment, device 100 can include an open nose portion 104 and rear portion 106 to allow it to be threaded onto insertion tool 200 and insertion tool 200 can also be used to initially distract the vertebral bodies. Optionally, the insertion tool 200 can include a single handle 201 and a gear system 203 where the handle 201 has an internal gear that, when turned, turns external gears on the shafts that turn the screws on the device 100 as depicted in FIGS. 33A-C.

Device 100 can be inserted with tapered nose portion 104 first. In one embodiment, a working channel of 8-26 mm is required for insertion of the device. One device 100 can be inserted, or, for additional support, two devices 100 can be inserted as shown in FIG. 5. Two devices 100 can be especially useful for treating larger patients in which the device may encounter higher loads. In another embodiment, three or more small devices can be inserted into the disc space in order to very accurately control the orientation and distance between discs. Three or more distraction mechanisms may be positioned circumferentially between two circular endplates to result in very accurate control and orientation of the end plates. Such a device would resemble a hexapod. In another embodiment, two or more devices may be mated or assembled in the disc space to work congruently in performing distraction either in height or width.

Figure 24:
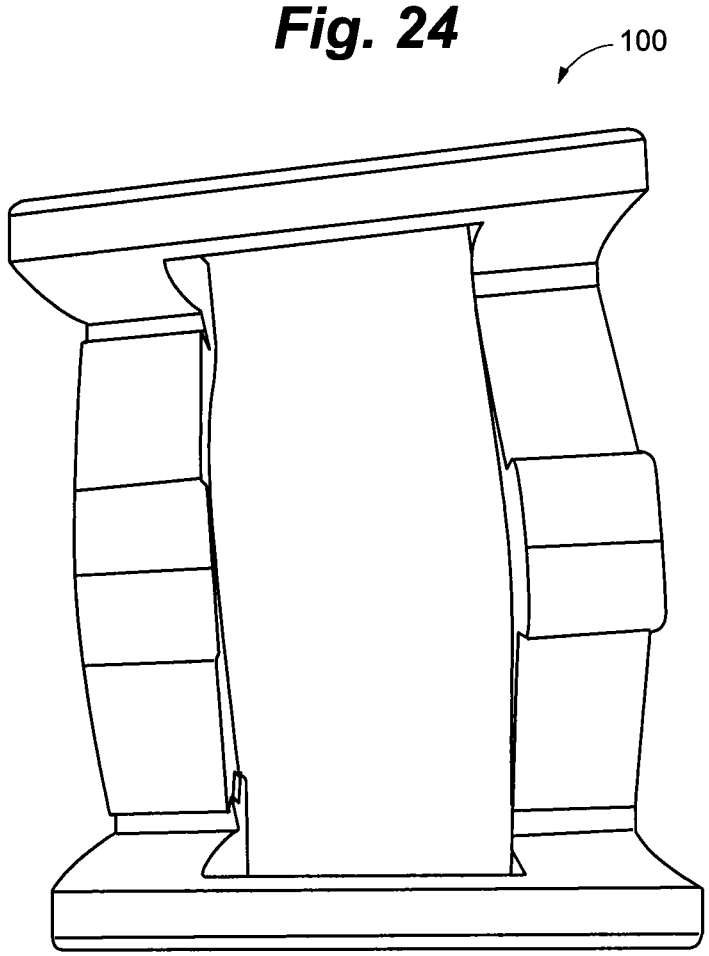
FIG. 24 is an end view of a distractible intervertebral body fusion device according to an aspect of the present invention.

Once inserted in the disc space, insertion tool 200 can be actuated to rotate drive screws 118. Drive screws 118 can be actuated from the rear of device 106 to allow insertion tool to reposition or, if necessary, remove device 100 prior to disengaging from device 100. Drive screws 118 can be actuated the same amount for uniform distraction on both sides of an embodiment with two drive screws or may be actuated different amounts for non-uniform distraction with one side of the device 100 higher than the other. Non-uniform distraction causes torsional forces on flexures. FIG. 24 depicts a device 100 have non-uniform distraction. Alternatively, an embodiment can be driven with a single flexure and single drive screw or with multiple flexures multiplexed to a single drive screw arrangement.

Unlike many common scissor jacks, such as, for example, car jacks, device 100 can easily be distracted from its lowest, or most compressed, state. This is because the flexure members 112 on each end of a given structural member are oriented such that the tensile loads on the flexures do not act towards each other, but instead pass by each other, like passing cars (see arrow A and arrow B in FIG. 1B). Common jacks, which do not utilize flexure members, may have difficulty distracting from the lowest state because the tensile loads can act "heads on" with each other, putting the device under strong internal horizontal compression but without a significant force component in the vertical direction at the lowest state that can easily initiate distraction. The tension in the flexure member required to support a compressive load is equal to the compressive load multiplied by the cosine of the angle of the rigid link divided by the sine of the rigid link. Because the sine of zero degrees, the angular position of normal scissor jacks in the compressed state, is equal to zero, the force required for initial distraction can be effectively very large. The rigid links of the device of various embodiments of the present invention may start off in the position of zero angular position, but because the flexure members are on opposing sides of the rigid links the effective angular position is non-zero, making the force required for initial distraction finite and generally smaller than a conventional scissor jack.

Figure 6:
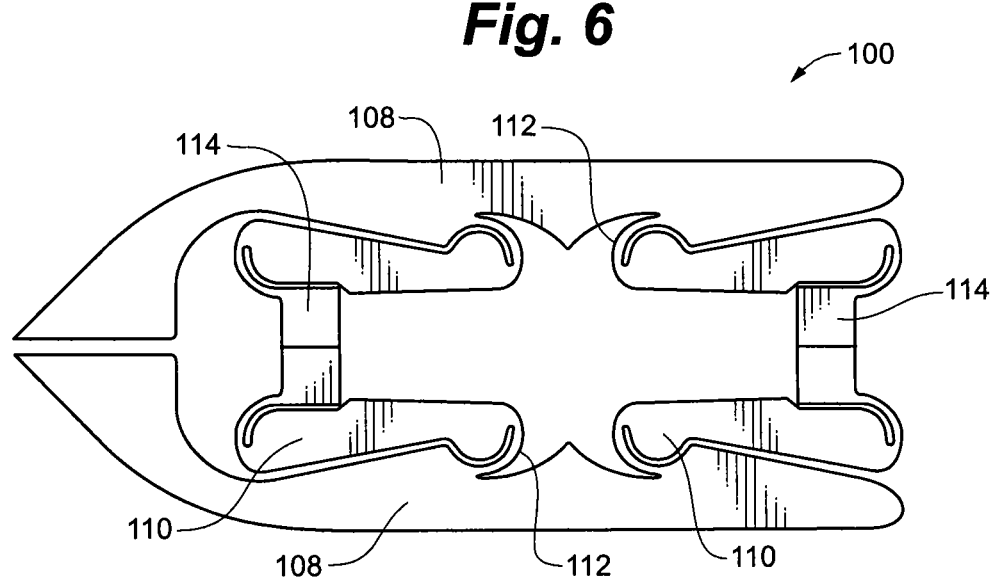
FIG. 6 is a side view of an embodiment of a distractible intervertebral body fusion device according to an aspect of the present invention.
Figure 8A:
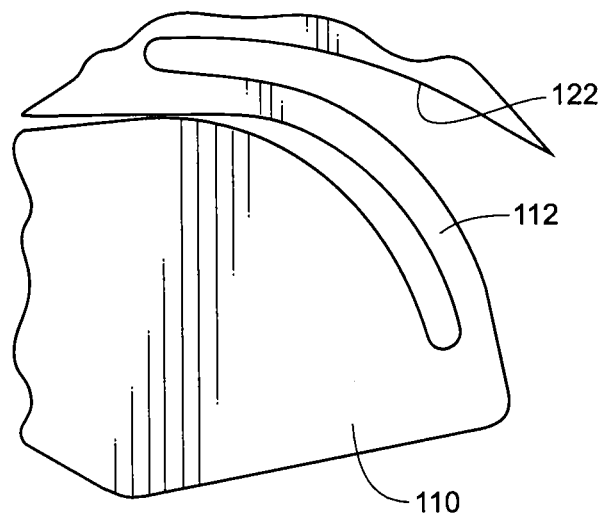
FIG. 8A is a partial view of a portion of an embodiment of a distractible intervertebral body fusion device according to an aspect of the present invention.
Figure 8B:
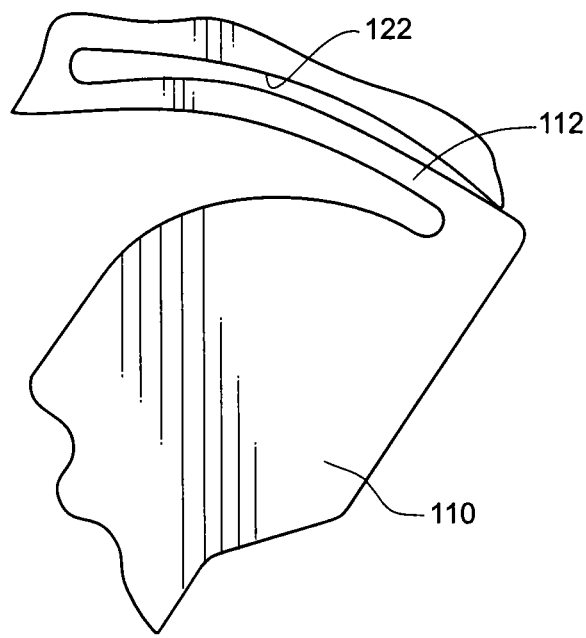
FIG. 8B is a partial view of a portion of an embodiment of a distractible intervertebral body fusion device according to an aspect of the present invention.
Figure 8C:
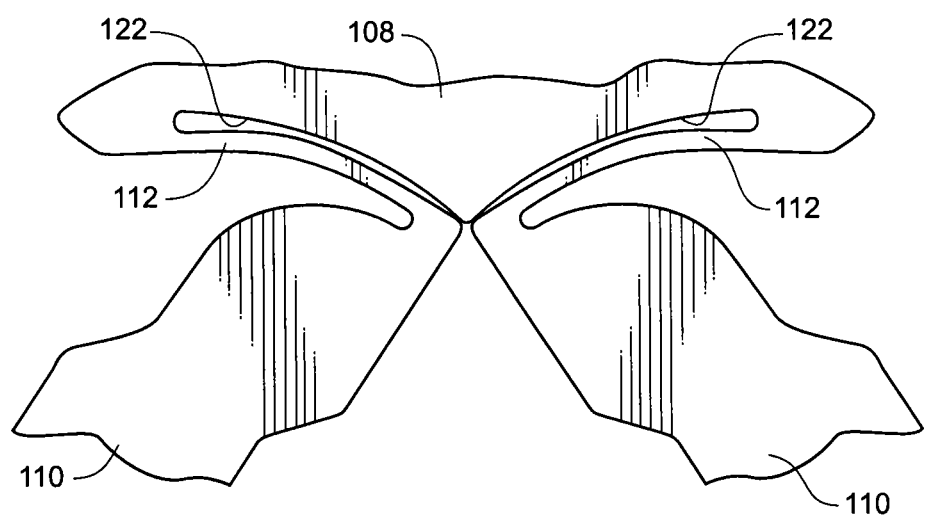
FIG. 8C is a partial view of a portion of an embodiment of a distractible intervertebral body fusion device according to an aspect of the present invention.
Figure 8D:
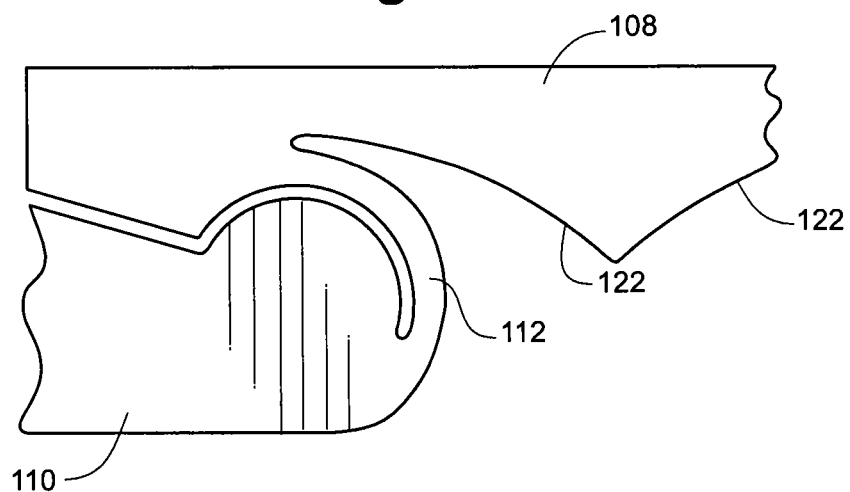
FIG. 8D is a partial view of a portion of an embodiment of a distractible intervertebral body fusion device according to an aspect of the present invention.

As drive screws 118 are actuated, the device 100 is distracted as shown in FIGS. 6 and 7. Drive screws 118 (not shown in FIGS. 6 and 7) drive expansion blocks 114 together, which cause flexure members 112 to deflect thereby expanding structural members 110 to distract end plates 108. Referring now to FIGS. 8A-8D, FIGS. 8A and 8D depict a flexure member 112 and structural member 110 before distraction, whereas FIGS. 8B and 8C depict after distraction. Each flexure member 112 begins wrapped around the curved end of the structural member 110. Note in FIG. 8A that the flexure 112 rests on the structural member 110. This allows the device 100 to carry a large compressive load in the compressed state without greatly deforming the flexure 112. As the structural members 110 are distracted, the flexure members 112 bend towards flat. In this embodiment, the flexure members 112 do not bend all the way flat, however, even at maximum distraction of the end plates 108, because they contact curved backstop 122. This allows the device 100 to carry a large compressive load in the distracted state without further deforming the flexure 112. Curved backstop 122 has a "frowning eyebrows" configuration in order to provide opposed curved surfaces for opposing flexure members 110. Because the flexure members 112 do not have to bend until they are completely flat to reach complete distraction, the amount of strain on the flexure members 112 necessary for complete distraction is minimized. The likelihood of device failure is therefore reduced.

Figure 8E:
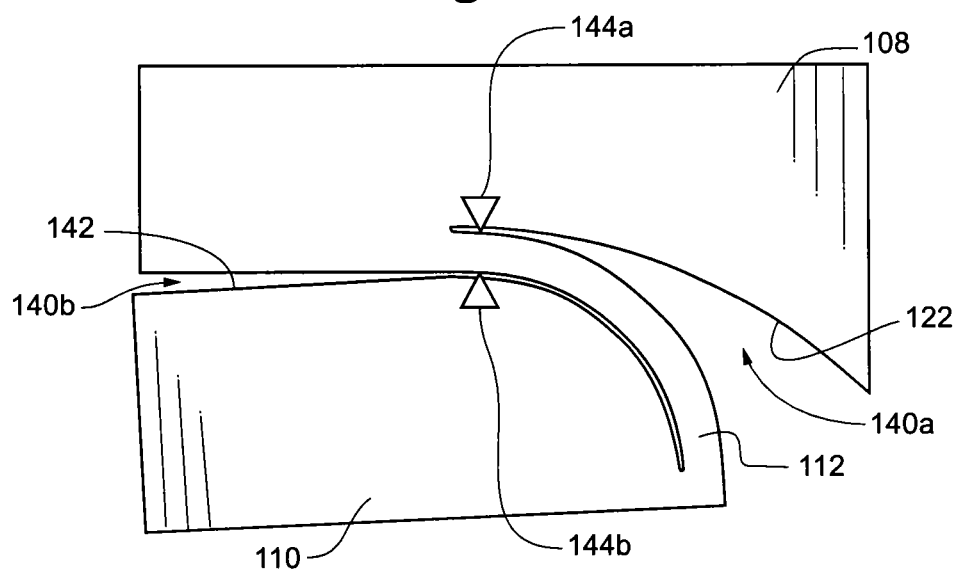
FIG. 8E is a partial view of a portion of an embodiment of a distractible intervertebral body fusion device according to an aspect of the present invention.
Figure 8F:
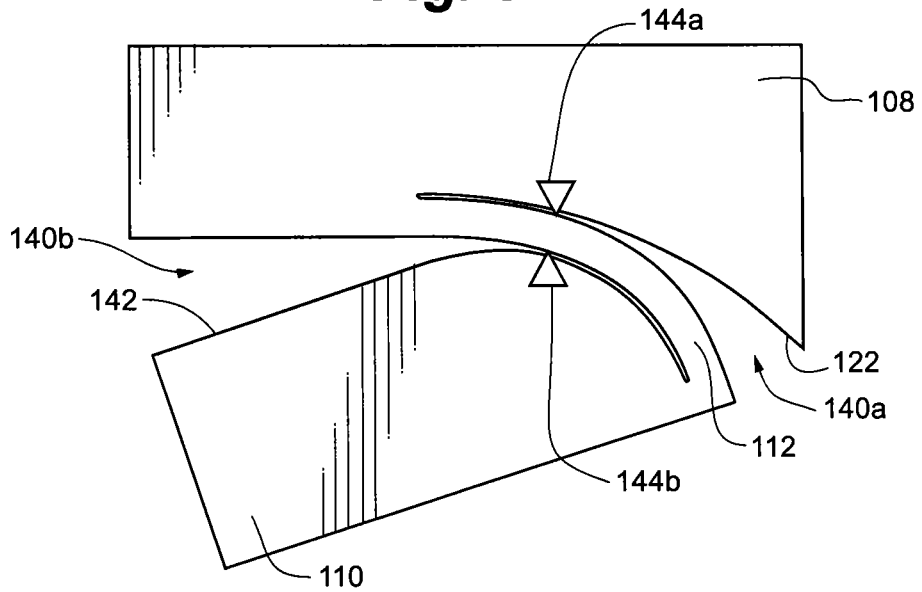
FIG. 8F is a partial view of a portion of an embodiment of a distractible intervertebral body fusion device according to an aspect of the present invention.
Figure 8G:
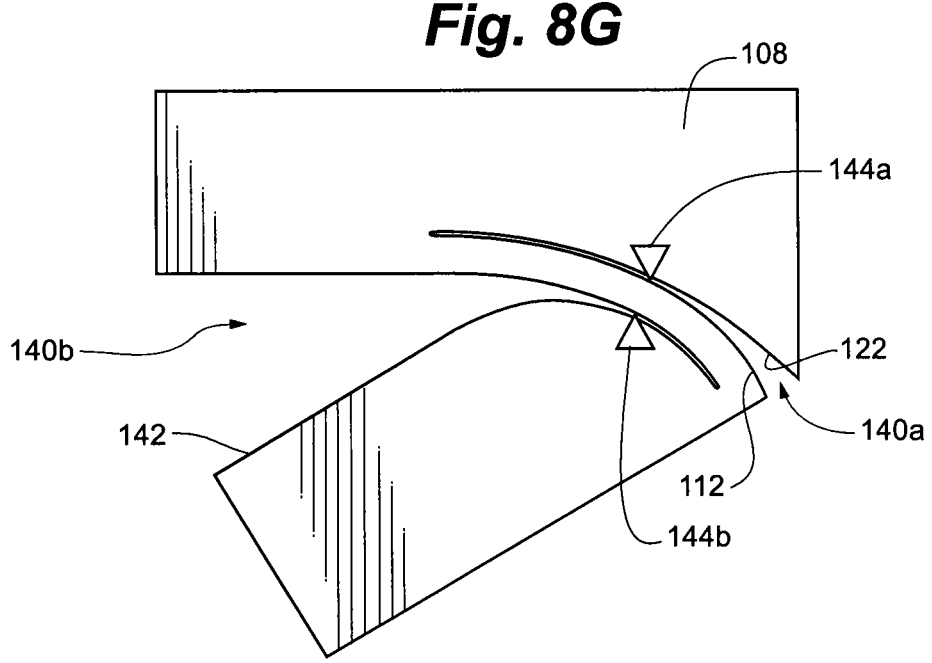
FIG. 8G is a partial view of a portion of an embodiment of a distractible intervertebral body fusion device according to an aspect of the present invention.

FIGS. 8E-8G depict the behavior of flexures as the device is distracted. Flexure member 112 defines a first open area, or kerf 140a, between curved backstop 122 and flexure member 112 and a second kerf 140b between inner perimeter 142 of structural member 110 and flexure member 112. When device 100 is in a collapsed configuration (FIG. 8E), kerf 140a is wider than kerf 140b. As device distracts, flexure member 112 flattens out towards curved backstop 122, so kerf 140b widens as kerf 140a narrows. The fulcrum around which flexure member 112 bends is shown by arrows 144a and 144b. As can be seen in FIGS. 8E-8G, the fulcrum 144a, 144b translates along the flexure member 112 as it bends. Fulcrum 144a, 144b therefore travels in both vertical and horizontal directions. This provides for increased distraction of the device. As the fulcrum 144a, 144b moves along the flexure member 112 as the device distracts, a greater portion of the compressive load on the device 100 is supported by the structural member 110 and, accordingly, the tensile forces on the flexure member 112 are reduced. The device 100 of this embodiment is therefore strongest when it is fully distracted.

Figure 9:
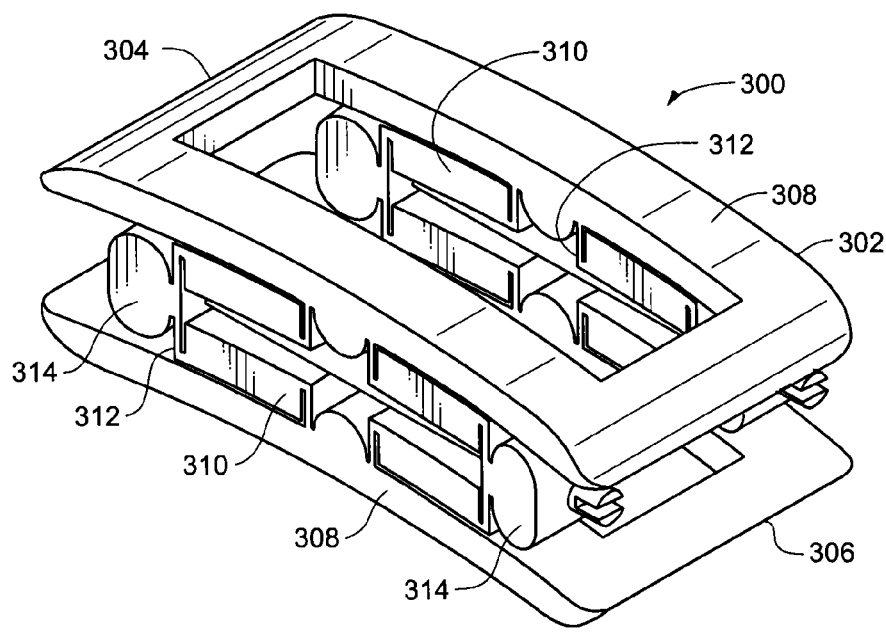
FIG. 9 is a side view of an embodiment of a distractible intervertebral body fusion device according to an aspect of the present invention.
Figure 10:
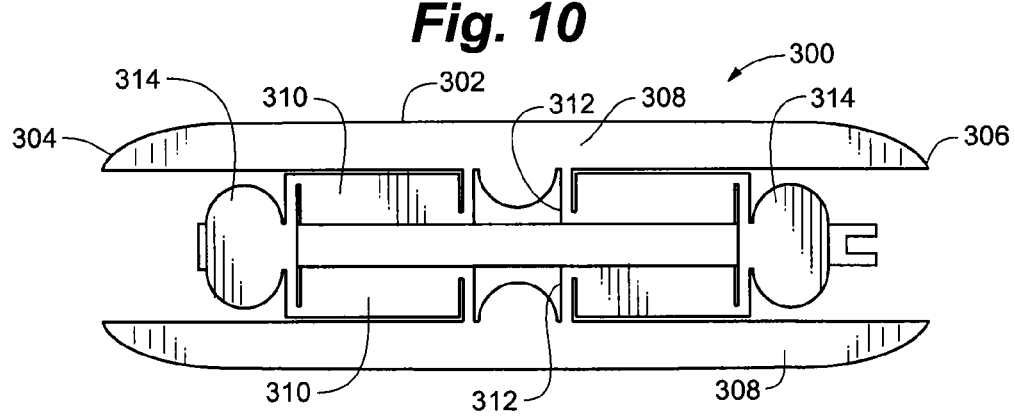
FIG. 10 is a perspective view of the distractible intervertebral body fusion device of FIG. 9.

Referring now to FIGS. 9 and 10, another embodiment of a distractible intervertebral body fusion device 300 is shown. Device 300 includes a device body 302 having a nose portion 304, a rear portion 306, a pair of opposed end plates 308, structural members 310, flexure members 312, and drive blocks 314. In some embodiments, as shown in FIGS. 9 and 10, nose portion 304 and rear portion 306 can be open. As described above, nose 304 and rear 306 portions can be used to accommodate an insertion tool for delivery of device 300.

Figure 11A:
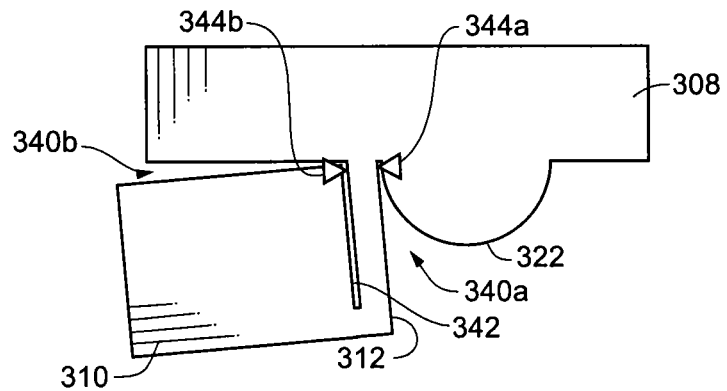
FIG. 11A is a partial view of a portion of an embodiment of a distractible intervertebral body fusion device according to an aspect of the present invention.
Figure 11B:
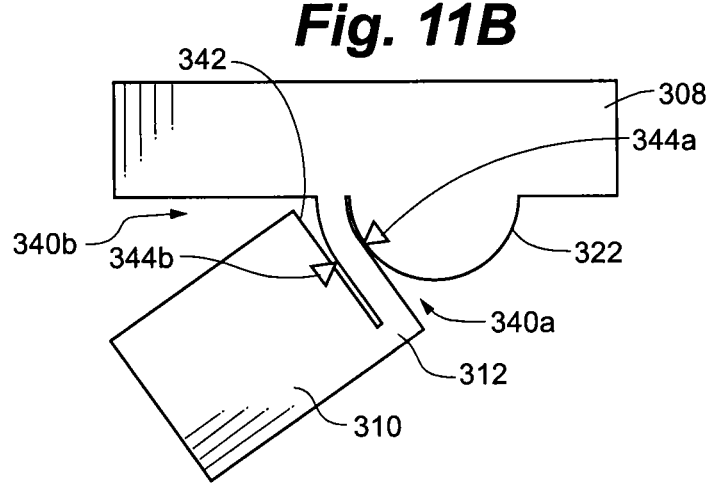
FIG. 11B is a partial view of a portion of an embodiment of a distractible intervertebral body fusion device according to an aspect of the present invention.
Figure 11C:
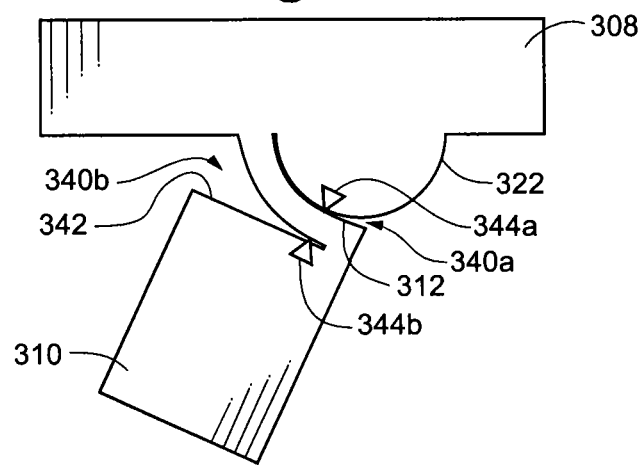
FIG. 11C is a partial view of a portion of an embodiment of a distractible intervertebral body fusion device according to an aspect of the present invention.
Figure 12:
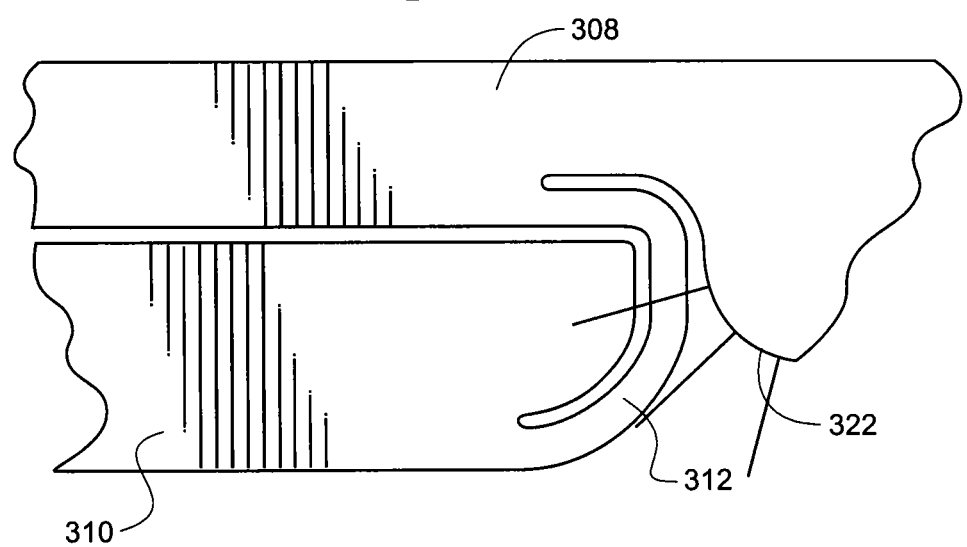
FIG. 12 is a partial view of a portion of an embodiment of a distractible intervertebral body fusion device according to an aspect of the present invention.

In the embodiment shown in FIGS. 9 and 10, drive blocks 314 and end plates 308 provide outwardly curved backstops 322 for flexure members 312 (in contrast to the inwardly curved backstops 122 depicted in the previous Figures). Flexures 312 curve around backstops 322 as the device 300 distracts as depicted in FIGS. 11A-11C. In the collapsed state shown in FIG. 11A, flexure member 312 is parallel to an inner surface 342 of structural member 310. As the device 300 distracts, flexure member 312 bends around backstop 322, widening kerf 340b and narrowing kerf 340a. As shown by arrows 344a, 344b, the fulcrum translates along the length of flexure member 312 (in both the horizontal and vertical directions) as the device distracts. Fulcrum 344a, 344b is always perpendicular to inner surface 342 of structural member 310. This results in the entire load on the device 300 being carried in compression by structural members 310. Therefore, there is little or no tensile force on flexure members 312. This allows flexure members 312 to be of a thickness or a material such that they enjoy an essentially infinite fatigue life. This embodiment allows device to be constructed from a material, such as nitinol, that provides strong compressive support when it is of large dimensions but that distorts easily when slender members of the same material are under tension or bending. FIG. 12 depicts a further flexure embodiment employing this principal. The flexure 312 in FIG. 12 is cut an additional length into end plate 308. This can help reduce the stress in the device and may improve fatigue life.

The thickness of the flexure 312 in relation to the bend radius of the curved backstop 322 determines the fatigue life of the flexure. In some embodiments, flexures can be configured and designed to have very long fatigue life. In one embodiment, a device made from nitinol having a thickness of the flexure members 312 that is preferably between 8% and 10% of the bend radius of the backstop 322, with a maximum thickness of 18% has an infinite fatigue life. In another embodiment, a flexure made from PEEK preferably has a thickness that is 4.5% to 6.4% of the bend radius, with a maximum thickness of 15%. In a further embodiment, a flexure comprised of annealed titanium can have a thickness of up to 18% of the bend radius. In other embodiments, flexures can be configured and designed to have a finite fatigue life associated with a predetermined range of maximum number of cycles of expansion and contraction.

Figure 13A:
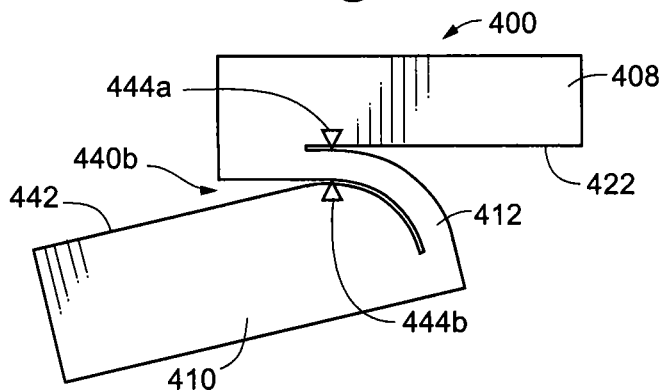
FIG. 13A is a partial view of a portion of an embodiment of a distractible intervertebral body fusion device according to an aspect of the present invention.
Figure 13B:
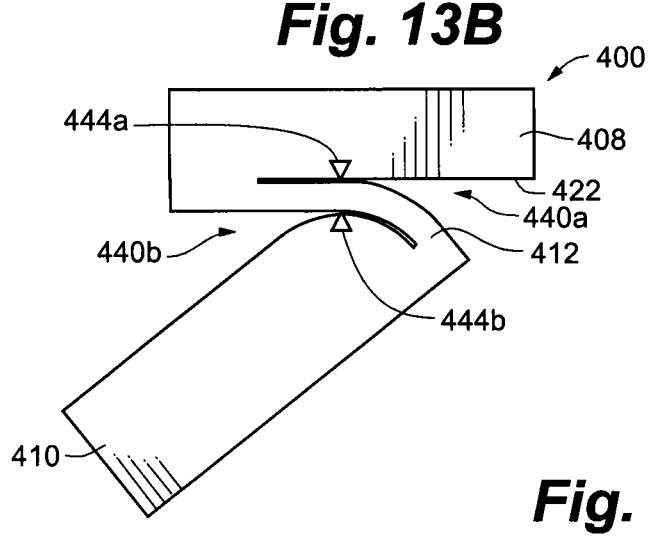
FIG. 13B is a partial view of a portion of an embodiment of a distractible intervertebral body fusion device according to an aspect of the present invention.
Figure 13C:
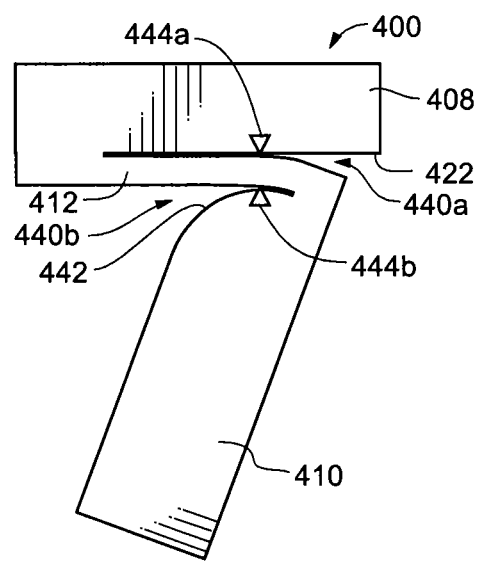
FIG. 13C is a partial view of a portion of an embodiment of a distractible intervertebral body fusion device according to an aspect of the present invention.

FIGS. 13A-13C depict a partial view of a distractible intervertebral body fusion device 400 including a further flexure embodiment. Backstop 422 on end plate 408 is flat. Flexure 412 begins curved around inner surface 442 of structural member 410 and flattens out, thereby widening kerf 440b and narrowing kerf 440a, as the device distracts. Fulcrum 444a, 444b again translates along flexure member 412 as the device distracts, providing increased distraction. As the device distracts, structural member 410 supports more of the load on device 400 in compression and less is supported by the flexure member 412 in tension.

In some embodiments, following distraction of the device, a bone growth stimulant, such as autograft, bone morphogenic protein, or bone enhancing material, may be delivered into device. In one embodiment, bone growth stimulant is delivered through a hollow chamber in insertion tool before insertion tool is disengaged from device. The device supports in-vivo loads during the time fusion occurs between the vertebral bodies and can support axial loads up to four times the weight of the patient. In one embodiment, openings in end plates allow for bone growth through the device.

Figure 25:
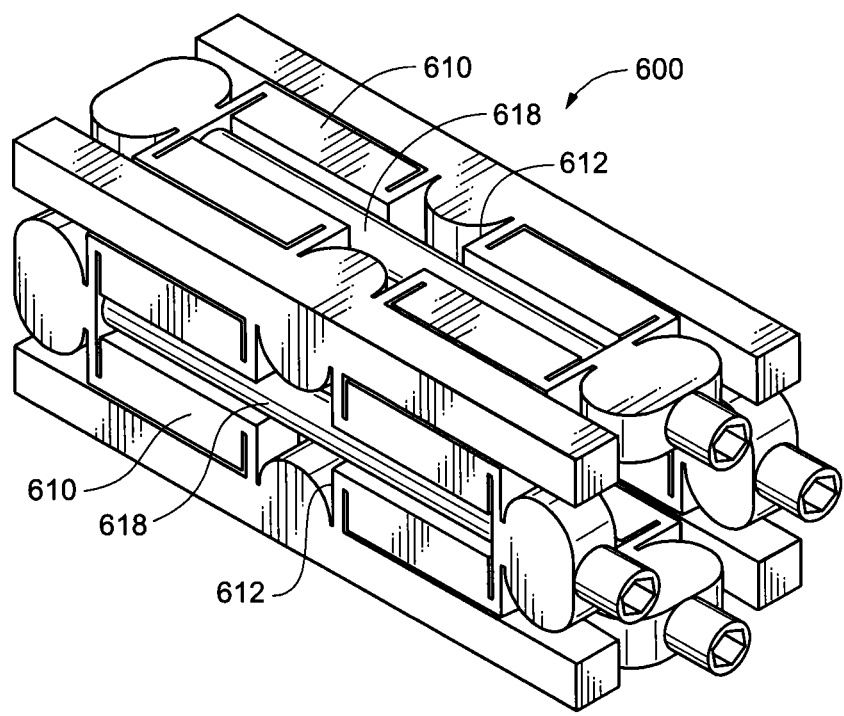
FIG. 25 is a perspective view of a distractible intervertebral body fusion device according to an aspect of the present invention.

As seen in FIGS. 6 and 7, some embodiments of the device can be distracted in only one direction, such as vertically. In other embodiments, the device can be distracted in two directions, such as both vertically and horizontally. In one embodiment depicted in FIG. 25, the device 600 can be distracted in both the vertical and horizontal directions. Device 600 includes a plurality of structural members 610 and flexures 612 on all four sides of the device 600. Separate drive screws 618 can be used to control horizontal and vertical distraction. In one embodiment, all drive screws can be controlled by a single drive member. This would provide for simultaneous horizontal and vertical distraction. In another embodiment as shown, each drive screw can be individually controlled in order to allow horizontal and vertical distraction to be performed independently. This device can be inserted through very small openings, which can then be made wider before being distracted taller. It is in this configuration that the device retains its compressive strength during and after vertical compression while being able to be distracted in the horizontal direction. Optionally, the screws that actuate horizontal expansion may be timed and driven together and the screws that actuate vertical expansion may be timed and driven together.

Figure 14:
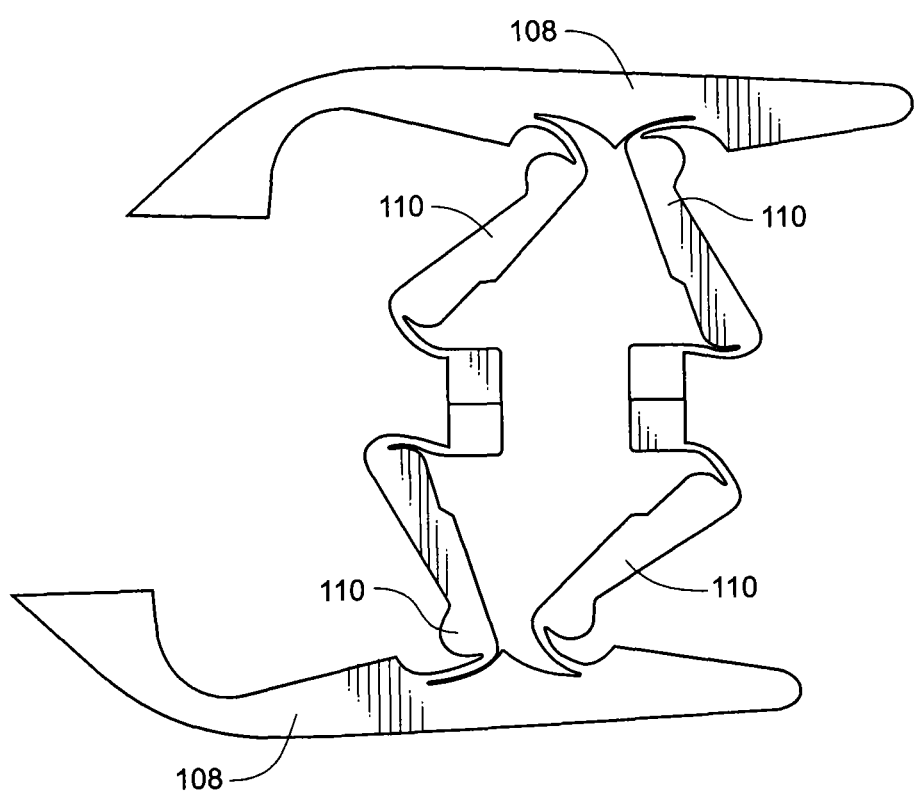
FIG. 14 is a side view of an embodiment of a distractible intervertebral body fusion device according to an aspect of the present invention.
Figure 15A:
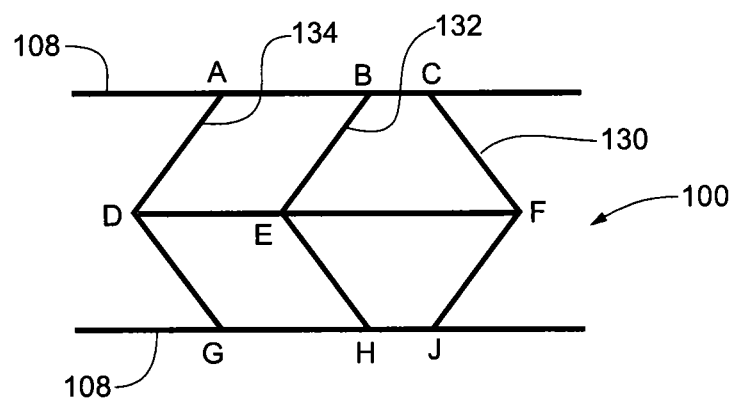
FIG. 15A is a simplified side view of an embodiment of a distractible intervertebral body fusion device according to an aspect of the present invention.
Figure 15B:
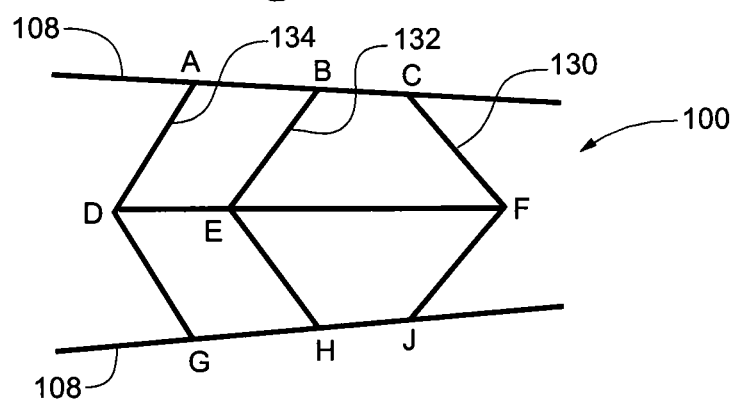
FIG. 15B is a simplified side view of an embodiment of a distractible intervertebral body fusion device according to an aspect of the present invention.

As noted above, a third strut may provide greater stability to certain embodiments of the device over a two-strut design. Referring to FIG. 14, excessive and/or uneven forces on a two-strut design can sometimes cause the device 100 to sublux as shown in FIG. 14. Subluxation causes the end plates 108, structural members 110 and, if during implantation, the drive screws 118, to become misaligned. This can cause collapse of the disc space and risks deformity. A third set of structural members may be added to provide stability to help support excessive and/or uneven loads and prevent subluxation. In addition, a third strut allows a physician, in some embodiments, the flexibility to control the parallelism of the end plates. As seen in FIG. 15A, the third strut 134 can be positioned apart from the first 132 and second 130 struts in order to maintain the end plates 108 completely parallel. However, in order to establish sagittal alignment, a physician may desire to maintain the end plates 108 in a non-parallel position. As can be seen in FIG. 15B, this can be accomplished by positioning the third strut 134 nearer to or farther from the other struts 130, 132 or by actuating the separate screw drives at separate rates. In this manner, a physician can configure the device 100 to maintain the end plates 108 in a non-parallel position to match the curvature of the spine. In one embodiment, the non-parallel position can be configured while the device is being implanted by using a drive mechanism that has the flexibility to adjust the position of the third strut 134 with respect to the second strut 132. The length of strut 134 may be different from that of strut 132 resulting in the end plates 108 being parallel during implantation but growing increasingly less parallel as the device is distracted.

Figure 19A:
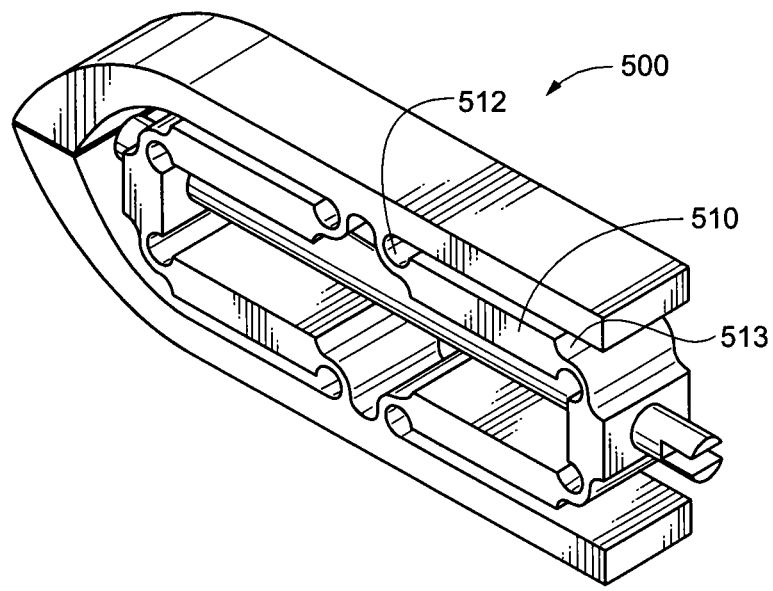
FIG. 19A is a perspective view of a distractible intervertebral body fusion device according to an aspect of the present invention.
Figure 19B:
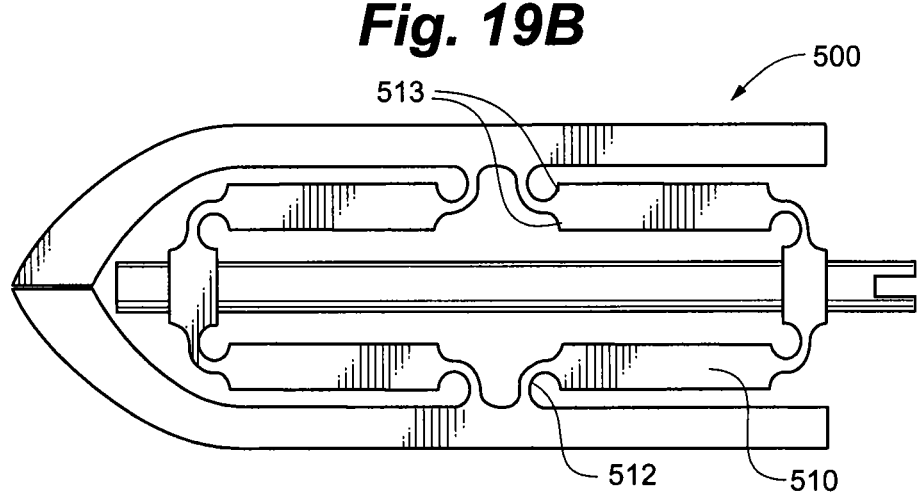
FIG. 19B is a side view of the distractible intervertebral body fusion device of FIG. 19A.
Figure 20A:
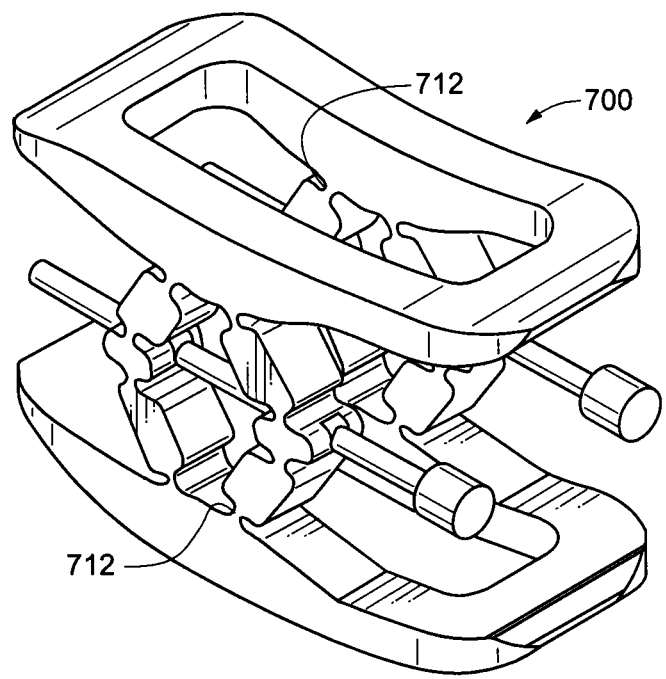
FIG. 20A is a perspective view of a distractible intervertebral body fusion device according to an aspect of the present invention.
Figure 20B:
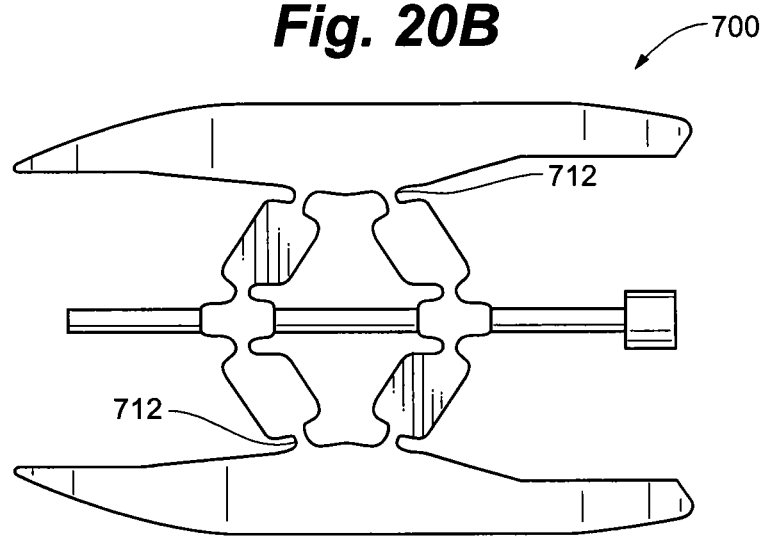
FIG. 20B is a side view of the distractible intervertebral body fusion device of FIG. 20A.
Figure 21A:
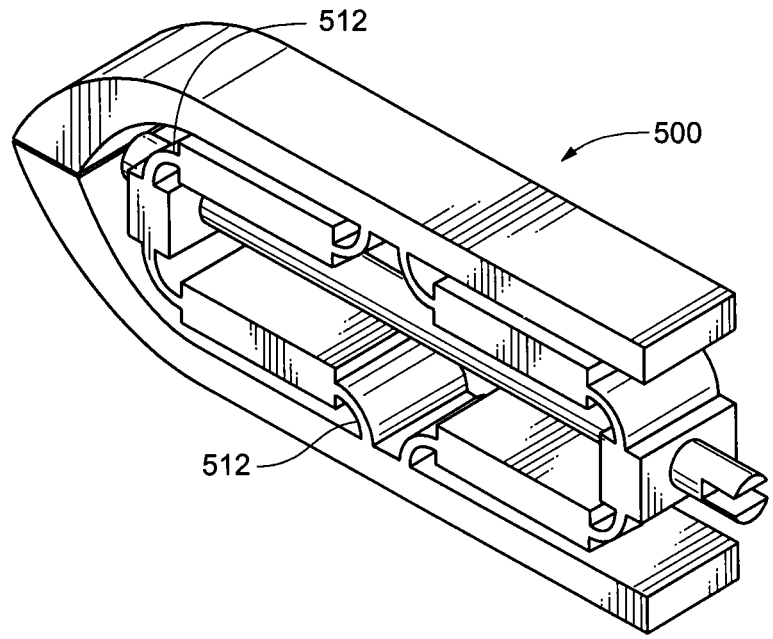
FIG. 21A is a perspective view of a distractible intervertebral body fusion device according to an aspect of the present invention.
Figure 21B:
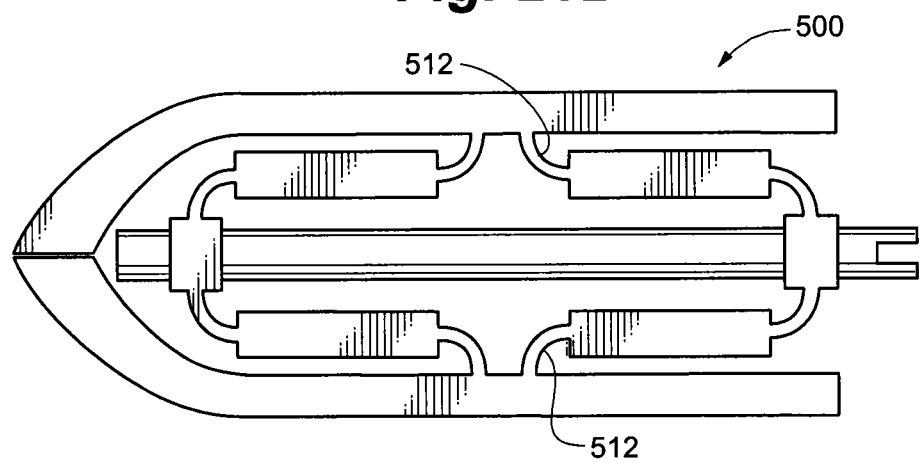
FIG. 21B is a side view of the distractible intervertebral body fusion device of FIG. 21A.
Figure 22A:
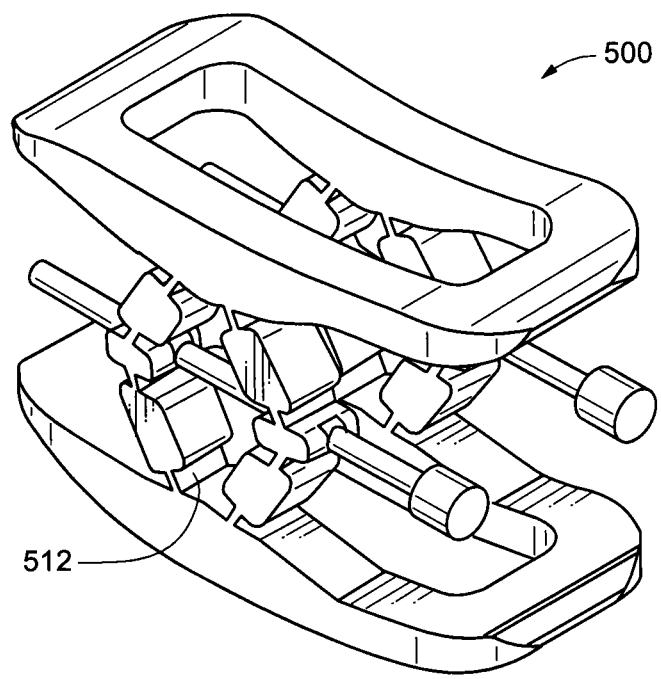
FIG. 22A is a perspetive view of a distractible intervertebral body fusion device according to an aspect of the present invention.
Figure 22B:
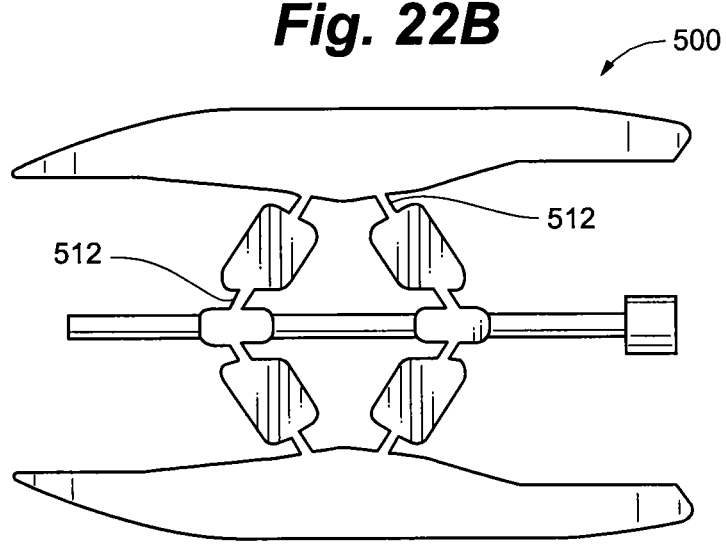
FIG. 22B is a side view of the distractible intervertebral body fusion device of FIG. 22A.

FIGS. 19A-19B depict a distractible intervertebral body fusion device 500 utilizing leaf flexures 512. This device includes small fillets 513 where the flexures 512 connect with the structural members 510. In this embodiment, no portion of the flexures 512 rests on the device body, so the entirety of any load on the device will be carried by the flexures. FIGS. 21A-21B and 22A-22B also depict devices 500 utilizing leaf flexures 512. In these embodiments, there are no fillets at the connection between the flexures 512 and the structural members 510. FIGS. 20A-20B depict a distractible intervertebral body fusion device 700 that utilizes elliptical flexures 712.

Figure 27A:
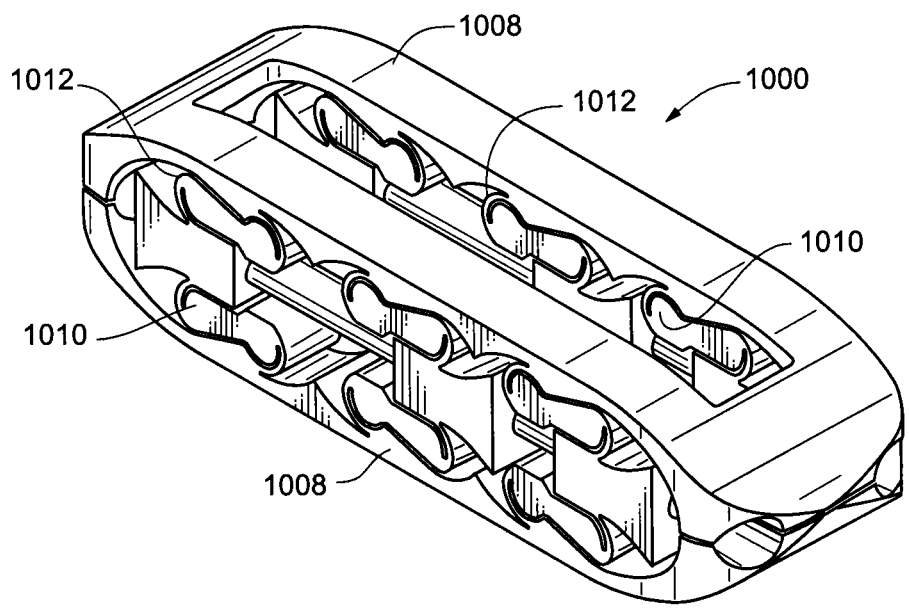
FIG. 27A is a perspective view of a distractible intervertebral body fusion device according to an aspect of the present invention.
Figure 27B:
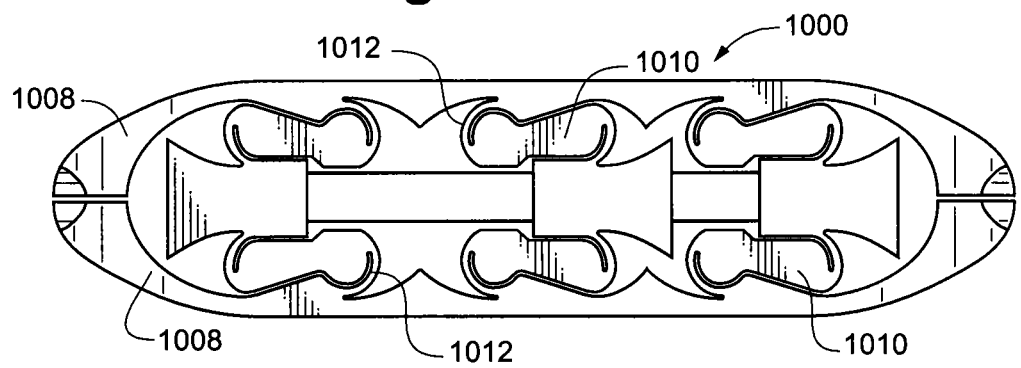
FIG. 27B is a side view of the distractible intervertebral body fusion device of FIG. 27A.
Figure 27C:
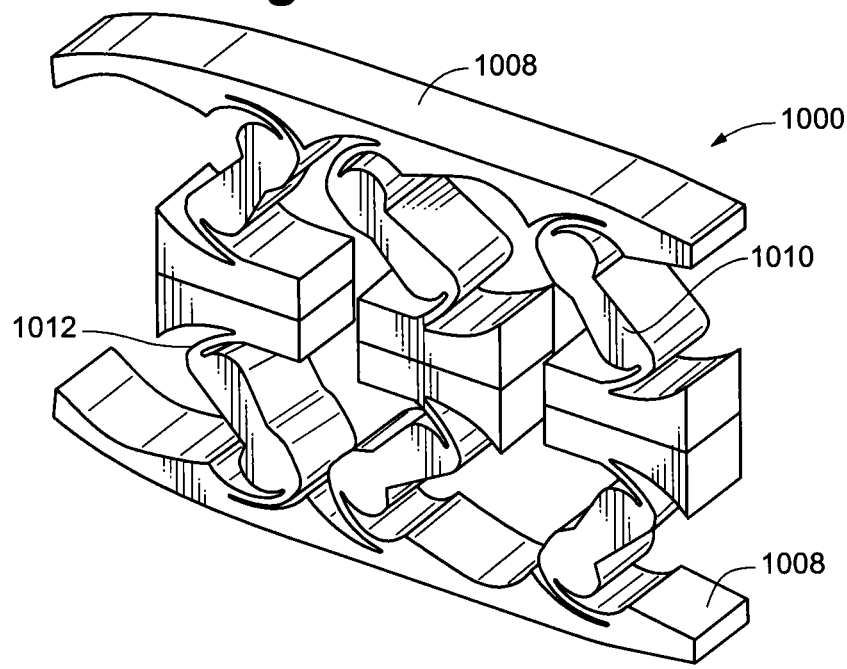
FIG. 27C is a simplified side view of the distractible intervertebral body fusion device of FIG. 27A.
Figure 27D:
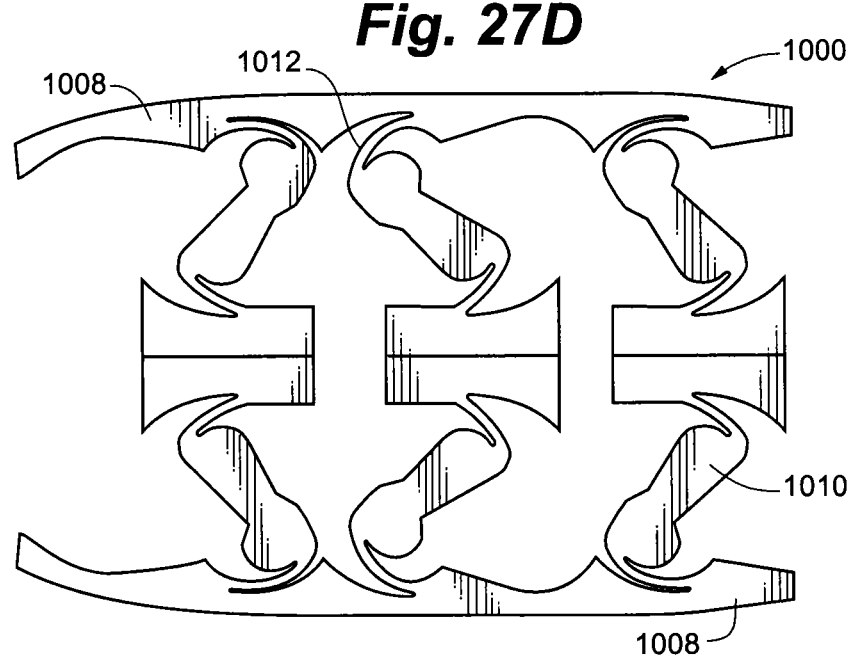
FIG. 27D is a simplified side view of the distractible intervertebral body fusion device of FIG. 27A.

FIGS. 27A-27D depict another embodiment of a distractible intervertebral body fusion device 1000 according to an aspect of the present invention. Device 1000 includes three sets of structural members 1010 on each side of the device 1000 and utilizes flexures 1012 similar to those depicted in FIGS. 8A-8G. The use of three sets of struts provides greater strength and helps avoid buckling or collapse of the device 1000. FIGS. 27C and 27D depicted a simplified view of the distracted device 1000 under a compressive load. The flexures 1012 in the middle of the device 1000 deform differently than the ones on each end due to the asymmetry of the device. The end plates 1008 of this embodiment are depicted as bending slightly under the compressive load. This is because the thickness of the end plates can be selected such that they are able to bend in-vivo to evenly distribute the supportive load of the device over the endplates of the vertebral bodies.

Figure 28A:
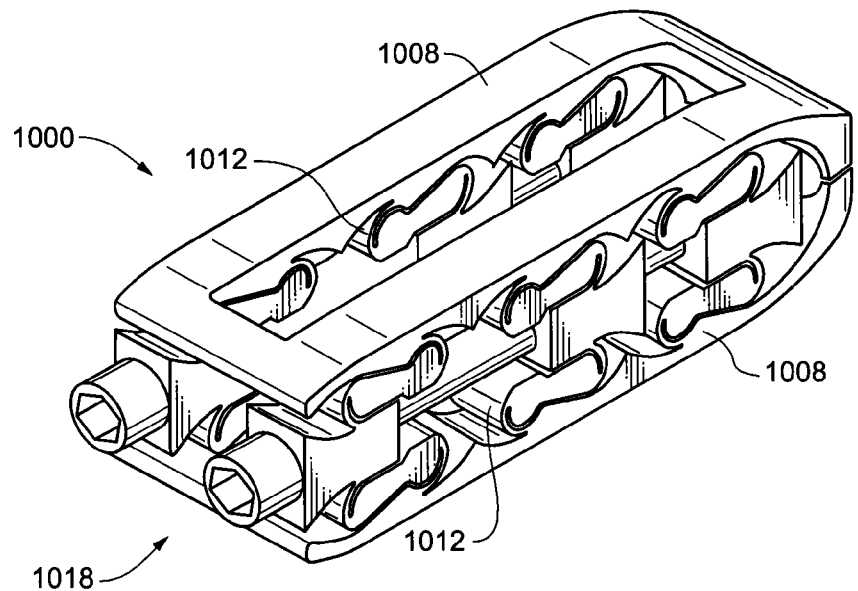
FIG. 28A is a perspective view of a distractible intervertebral body fusion device according to an aspect of the present invention.
Figure 28B:
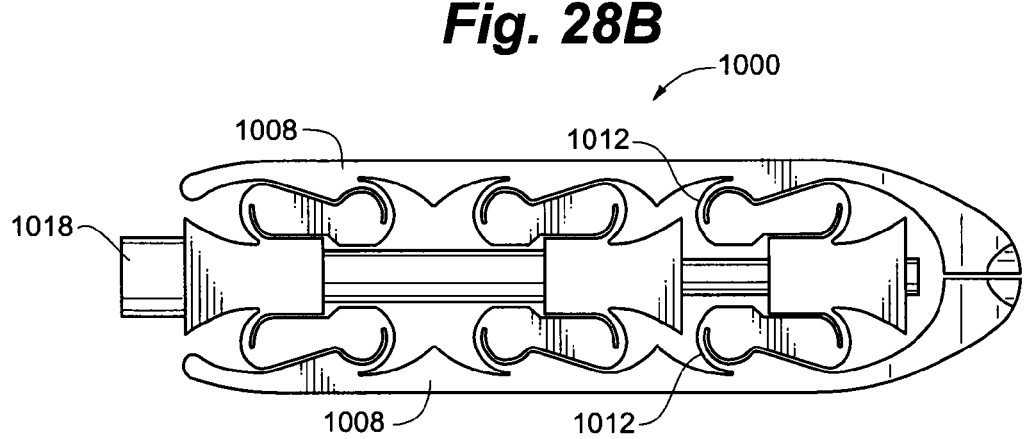
FIG. 28B is a side view of the distractible intervertebral body fusion device of FIG. 28A.
Figure 29A:
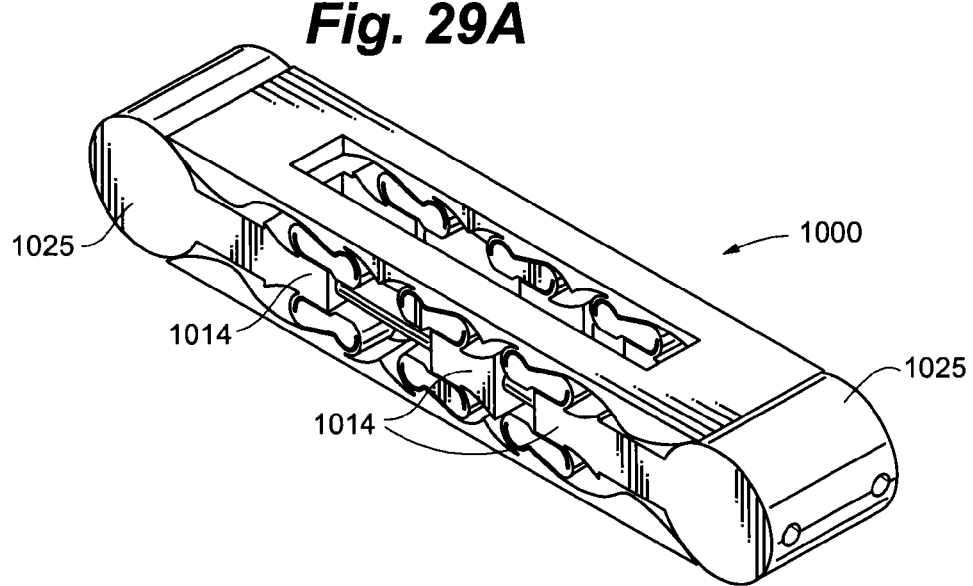
FIG. 29A is a perspective view of a distractible intervertebral body fusion device according to an aspect of the present invention.
Figure 29B:
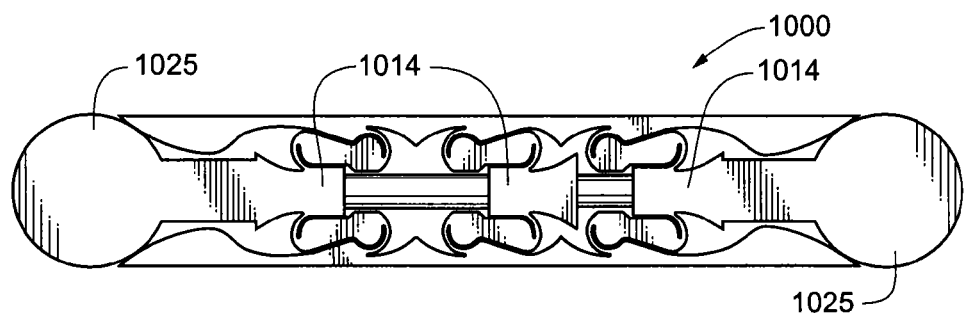
FIG. 29B is a side view of the distractible intervertebral body fusion device of FIG. 29A.
Figure 30A:
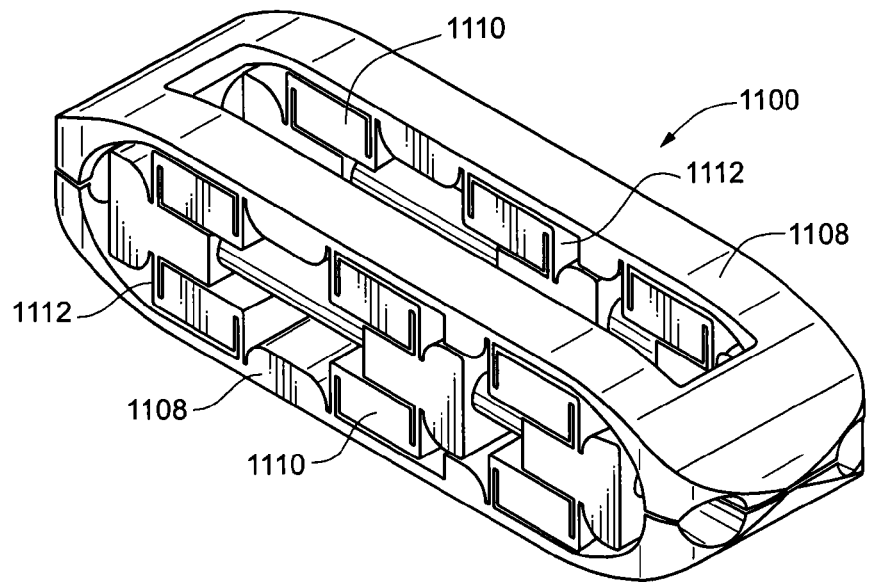
FIG. 30A is a perspective view of a distractible intervertebral body fusion device according to an aspect of the present invention.
Figure 30B:
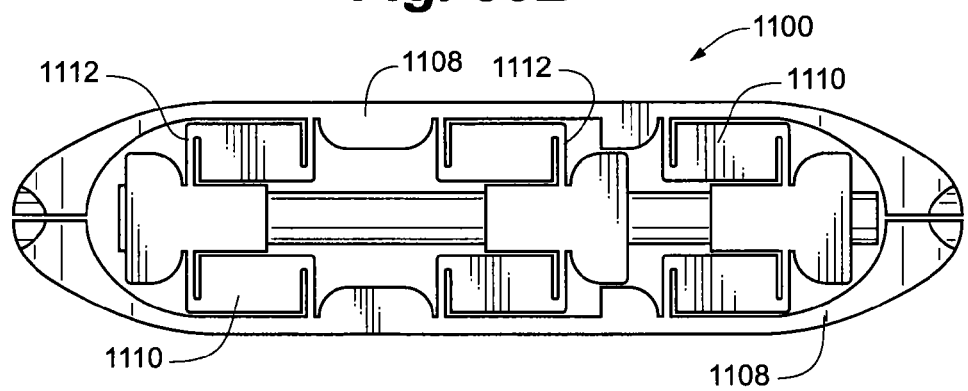
FIG. 30B is a side view of the distractible intervertebral body fusion device of FIG. 30A.
Figure 30C:
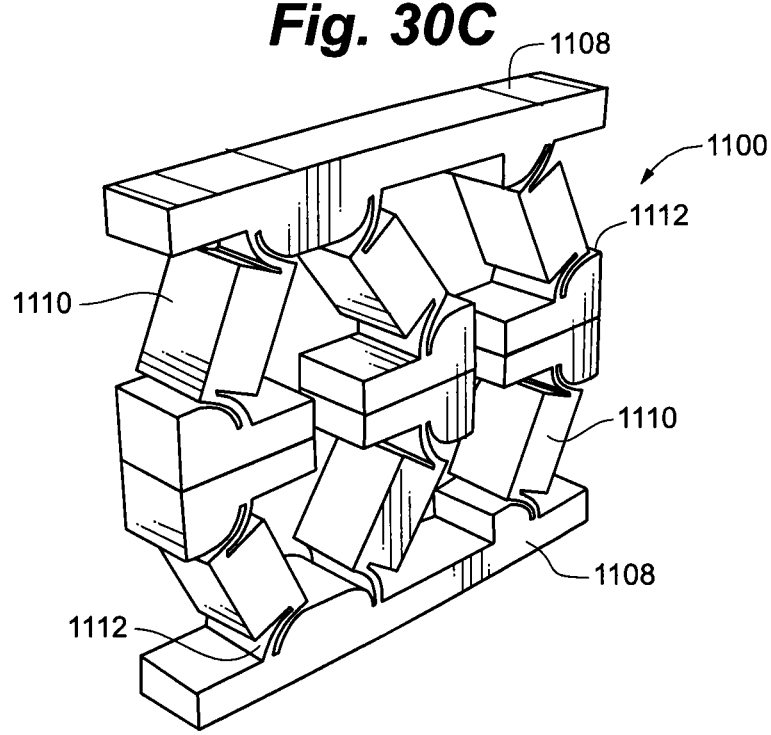
FIG. 30C is a simplified side view of the distractible intervertebral body fusion device of FIG. 30A.
Figure 30D:
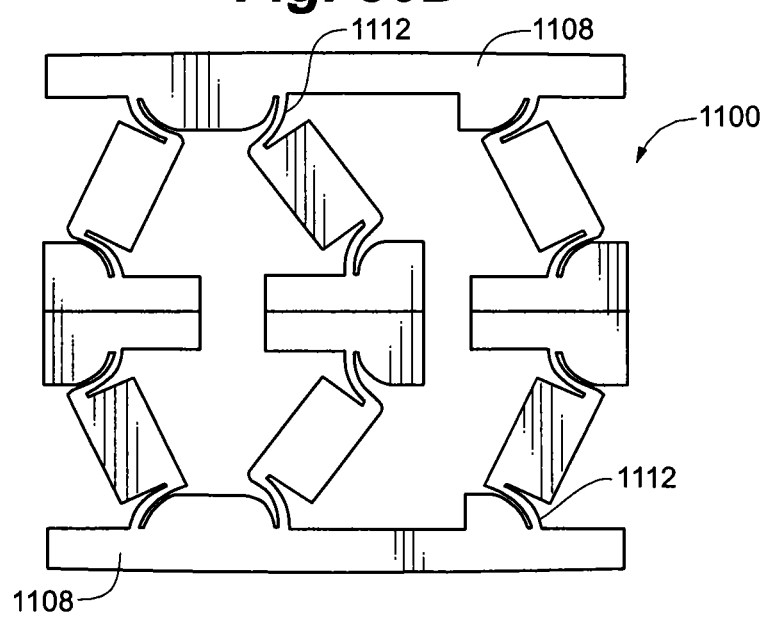
FIG. 30D is a simplified side view of the distractible intervertebral body fusion device of FIG. 30A.

FIGS. 28A and 28B depict a variation of the device 1000 of FIGS. 27A-27D having a differential screw drive 1018. This allows the flexures 1012 on each side of the device to be driven at different rates, so that one can control the angle of the device's end plates 1008 once the device 1000 is distracted. FIGS. 29A and 29B depict a further variation of the device 1000 that includes a wedge 1025 on each end for driving the blocks 1014 together to distract the device 1000. The wedges 1025 provide a greater level of compressive strength to the device 100 once it is distracted than the flexures 1012 do alone. The wedges 1025 also reduce the potential for the device to sublux. The wedges 1025 may be shaped or sized such that the device is primarily supported by the flexures and has the ability to sublux slightly but not fully.

Another embodiment of a distractible intervertebral body fusion device 1100 according to an aspect of the present invention is depicted in FIGS. 30A-30D. This embodiment uses flexures 1112 similar to those shown in FIGS. 11A-11C. As with device 1000, the middle flexures 1112 of device 1100 deform differently than the ones on each end due to the asymmetric sets of structural members 1110. In this embodiment, the end plates 1108 are thicker and do not deform under the compressive load.

Figure 31A:
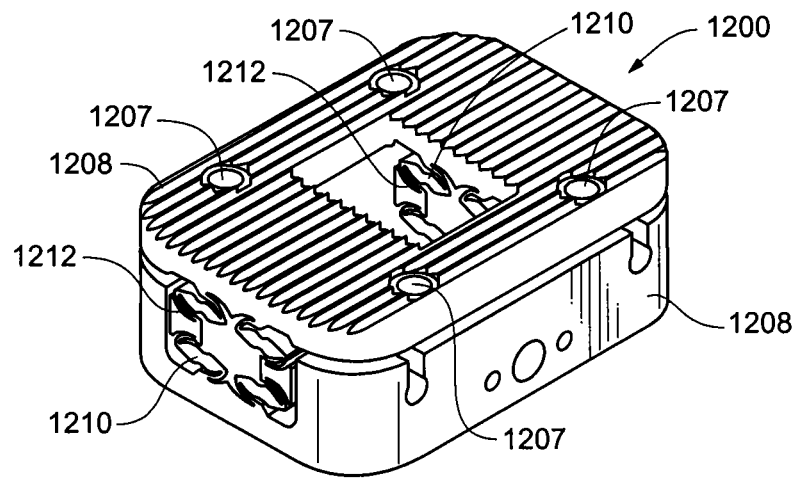
FIG. 31A is a perspective view of a distractible intervertebral body fusion device according to an aspect of the present invention.
Figure 31B:
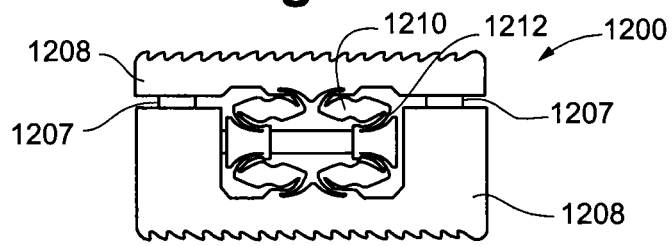
FIG. 31B is an end view of the distractible intervertebral body fusion device of FIG. 31A.
Figure 31C:
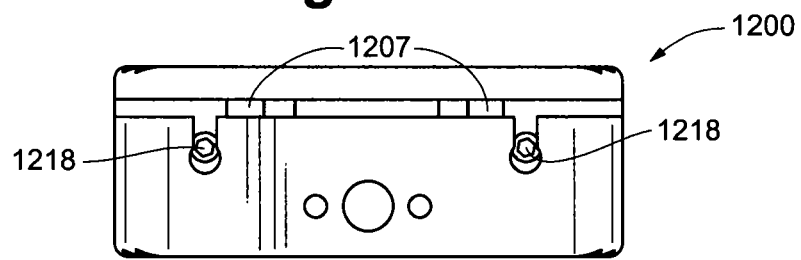
FIG. 31C is a side view of the distractible intervertebral body fusion device of FIG. 31A.
Figure 32A:
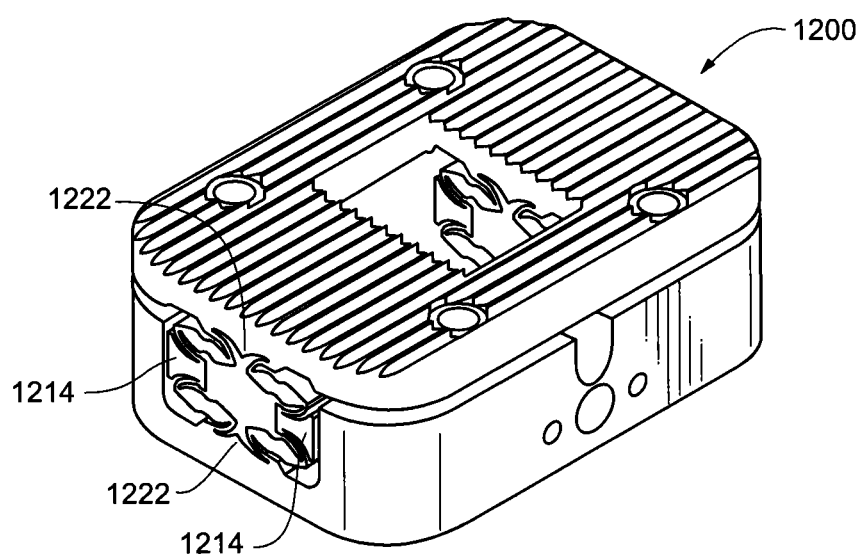
FIG. 32A is a perspective view of a distractible intervertebral body fusion device according to an aspect of the present invention.
Figure 32B:
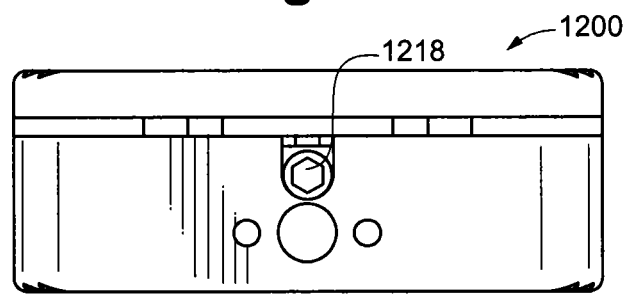
FIG. 32B is an end view of the distractible intervertebral body fusion device of FIG. 32A.

Another embodiment of a distractible intervertebral body fusion device 1200 according to an aspect of the present invention is depicted in FIGS. 31A-31C. The device 1200 includes two sets of structural members 1210 and flexures 1212 on each side of the device 1200. The device 1200 includes four distractible pins 1207 extending between the end plates 1208 that resist torsional forces on the device 1200. The pins 1207 also limit the device to movement in the vertical direction and eliminate the possibility of subluxation. A pair of drive screws 1218 can be used to distract the devices. FIGS. 32A and 32B depict a variation of the device 1200 that utilizes a single drive screw 1218. FIGS. 32A and 32B also depict an embodiment where the blocks 1214 and the backstops 1222 that create the "frowning eyebrows" have been added as separate parts in order to dramatically thin the kerf that is present in earlier embodiments. The thinning of the kerf will reduce local stresses and strains in the flexures and increase the fatigue life.

In various embodiments, distractible intervertebral body fusion device has a one-piece device body that can be manufactured in a distracted or partially distracted state. This provides great cost savings over devices that require multiple pieces to be separately manufactured and assembled. Manufacturing in the distracted state provides additional clearance for assembly and for access by manufacturing tools, the size of which is inversely proportional to the cost of manufacturing. In addition, when the device is manufactured in the distracted state, the device can be compressed into a position of minimal height while compressive stress remains in the flexure members. This compressive stress results in a negative mean stress, which can extend the fatigue life of the device. In one embodiment, the device can be manufactured using wire or sink edm. In another embodiment, the device can be manufactured using three-dimensional printing techniques or the like. In some embodiments, portions of the flexures can be machined separately and welded to the device. This allows for flexures that have zero kerf and rest completely against the backstops once distracted.

In one embodiment, the surface of the device can be treated to minimize surface roughness or to reduce pitting of the material within the body. A rough surface or pits can increase the stress on the device, which can result in shortening of the fatigue life and/or reduce fatigue strength. In one embodiment, the surface can be treated with electro-polishing. In another embodiment, the surface can be left untreated because a rough surface on the end plates helps prevent accidental extrusion of the device. In one embodiment, the device can also be coated with a highly elastic, impermeable material to extend its fatigue life. Specifically, the impermeable material would prevent the corrosive properties of blood from degrading the device. In another embodiment, the device can be comprised of a biocompatible material, so that no coating is necessary. In a further embodiment, the device can be made of a biodegradable material designed to degrade in the body at a selected stage of the healing process, such as after bone fusion.

Numerous other types of supports may be used with the device. Supports can be used to supplement the compressive strength, bending, or torsional strength of device. In one embodiment, one or more rigid supports can be inserted into the open space between end plates after distraction to help keep the end plates in their distracted state. In another embodiment, chocks can be placed at the intersection of structural members in each strut to provide further support for struts. In a further embodiment, a rod and screws can be used with the device as part of an assembly affixed to the vertebral body.

Figure 26A:
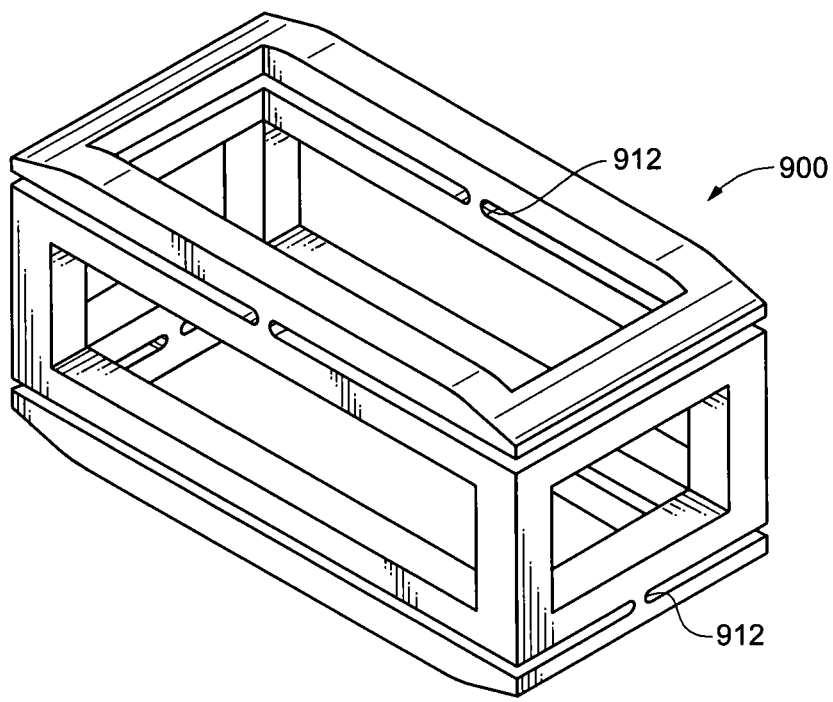
FIG. 26A is a perspective view of a distractible intervertebral body fusion device according to an aspect of the present invention.
Figure 26B:
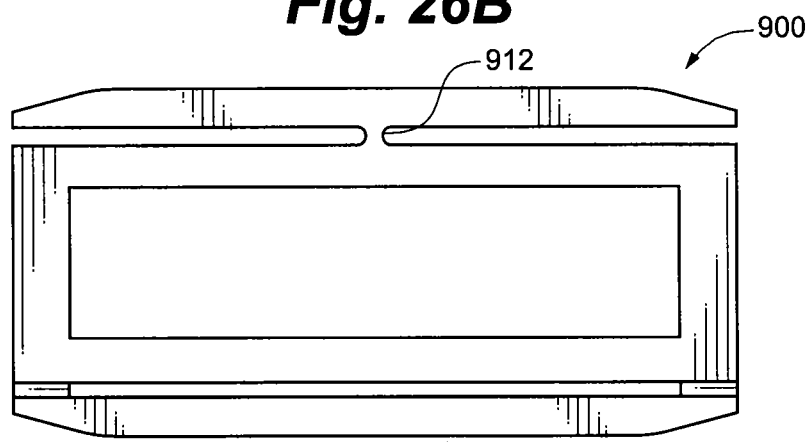
FIG. 26B is a side view of the distractible intervertebral body fusion device of FIG. 26A.

In another embodiment distractible intervertebral body fusion device 900, shown in FIGS. 26A-26B, can comprise a rigid cage capable of tilting front to back and/or side to side. Flexures 912 and/or springs can be oriented around the periphery of the device to allow for tilting in a variety of axes. A device capable of tilting can be beneficial in that providing additional degrees of flexibility built into the device can promote bone growth, distribute stress across the surface of the end plates, and allow the device to adjust to the curvature of an individual's spine.

In a further embodiment, the struts comprising structural members, flexures, and blocks can be replaced with large flexures extending between the end plates. Such a device can be non-distractible and can be provided in different sizes for insertion into variously sized disc spaces.

A device in accordance with the various embodiments can be used for a variety of intervertebral fusion applications, including, for example, cervical, thoracic anterior lumbar, trans-foraminal lumbar, extreme lateral lumbar, and posterior lumbar. In one embodiment, device can be inserted at 6 mm height and distracted to 14 mm for cervical applications and can be inserted at 7 mm and distract to 16 mm for other applications. Prototypes of this device have successfully demonstrated distraction to 220% of the original height. Scissorjacks of the prior art designed for distraction of vertebral bodies are capable of distracting to only less than 200% of the original height.

Various embodiments of implantation procedures for these applications may be as follows:

Cervical: The device is implanted via an anterior approach at the C3 to C7 levels using autograft. The device is used with supplemental anterior plate fixation.

Trans-foraminal lumbar: The device is implanted via a posterior approach from the L2 to S1 levels using autograft. The device is used with supplemental posterior rod fixation.

Posterior lumbar: The device is implanted via a posterior approach from the L2 to S1 levels using autograft. Two devices are implanted; one on the left side of the disc space and the other on the right side of the disc space. The device is used with supplemental posterior rod fixation.

Anterior lumbar: The device is implanted via an anterior approach from the L3 to S1 levels using autograft. The device is used with supplemental anterior plating fixation of posterior rod fixation.

Extreme lateral lumbar: The device is implanted via a lateral approach from the T12 to L4 levels using autograft. The device is used with supplemental posterior rod fixation.

In another embodiment, the device can be used in vertebral body replacement. After resection of a vertebral body or multiple vertebrae due to fracture or tumor, the device can be distracted to bridge two separate vertebrae. The distracted device bridges and supports the void left after resection. The device can be constructed in different sizes to accommodate the size difference of cervical, thoracic and lumbar vertebrae.

In another embodiment, the device can be used as an interspinous distraction device. The device can be placed between two adjacent spinous processes through a minimal access system. The device can be inserted in a collapsed configuration to allow ease of placement. Once in position, the device can be actuated to lock the vertebrae in a distracted position. The device can have gripping teeth at the point of contact with the spinous processes to help fix it in place.

In another embodiment, device can be used for interspinous fusion. The device can be placed between two adjacent spinous processes through a minimal access system in a collapsed configuration. Once in position, the device can be actuated to lock the vertebra in a distracted position. The device can have a bolt locking mechanism to lock the device in the distracted position and to lock the locking plates through the spinous processes. The device can also have gripping teeth on the outside to help keep it in place. Autograft or bone fusion enhancing material can be placed in the open space in device.

In another embodiment, device can be used for intervertebral disc replacement. The device can be placed in a disc space after removal of the nucleus pulposus. The device can then be distracted to the proper disc space height for the type of vertebra—cervical, thoracic, or lumbar. The device then functions as a mechanical annulus fibrosis. The device can be used on its own or in combination with a nucleus pulposus implant or soft posterior rodding system. A PEEK or biogel nucleus pulposus implant can be placed into the open area in the device after it is distracted. The implant and device will function as a mechanical disc device. The device can be constructed of a flexible material having similar properties to that of a human disc.

In another embodiment, the device can be used as a distractible cage for osteoporotic bone. The device can be constructed of a material with a modulus similar to that of bone and can be coated with a hydroxyappetite to enhance bone formation in the patient.

In another embodiment, the device can be used in flexure member facet joint replacement. After resection of a hypertrophic facet joint, the device can be actuated and subluxed. Each subluxed plate can be fixed to adjacent vertebrae with a pedicle screw. This will allow motion similar to that of a facet joint and prevent instability. The device can be part of a soft fusion device system and can be used in combination with an intervertebral disc replacement device.

In another embodiment, the device can be used as a programmable distraction cage with a dynameter and bone stimulator. A programmable micro-machine actuator device can be implanted within the device. The device is distracted during implantation and can provide force readings through a radio frequency communicator post-surgery. The shape of the device can be altered while it is implanted by distracting the end plates with the actuator device, which can result in lordosis, kyphosis, further distraction, or less distraction. In one embodiment, a battery device powers the system and can also form a magnetic field that works as a bone stimulator. The battery life may be limited to a short period of time, such as one week. Small movements of the device can be used to generate electrical energy with piezo-electrics or conducting polymers that may be used to recharge the batteries, capacitors, or other such power storage devices. Alternatively, the device may be powered through an RF inductive or capacitively coupled arrangement.

In another embodiment, the device can be a self-actuating distractible cage. The device can be inserted into the disc space in a collapsed state. Once the device is released, it can slowly distract to a preset height. In this embodiment, the distraction may be driven by spring action of the flexures.

In another embodiment, the device can be used in facial maxillary surgery as a fracture lengthening device for mandibular fractures. The device can be designed with narrow end plates having perpendicular plates with holes that allow fixation of each plate to either a proximal or distal fracture. The device can be actuated through a slow spring action flexure mechanism to a preset height. This will allow lengthening of the defect in cases of fracture bone loss, dysplasia, or hypoplasia.

In another embodiment, device can be used in orthopedic applications as a lengthening nail for distraction of long bone fractures. After an orthopedic fracture occurs with bone loss, a distractible elongating nail can be placed to lengthen the bone. The elongation occurs over a few days with micrometer movements. This application will involve a distraction device inserted in between the moving portion of the nails exerting counter-distraction forces, which will provide lengthening of the bone.

In another embodiment, device can be used in a gastric band application. Present gastric bands have an inner tube rubber diaphragm that is constricted via tubing attached to a small reservoir placed superficially under the skin in an accessible area. The constriction mechanism requires an injection of saline into the reservoir by a surgeon a few times a year. A flexure embodiment will include an elliptical device having two flexure members that constrict the center by opposing distraction forces. The device will be open on one end to allow placement around the upper portion of the stomach. The device can include a programmable micro-machine to actuate the flexure members. The device can also measure stomach fundus pressures and diurnal variations in the size of the stomach.

In another embodiment, the flexure device can be used to replace phalangeal joints in the hand, metatarsal joints in the foot, or calcaneal-talus joints. These joints can have flexural members implants that will allow motion of adjacent bones and limit hyper-extension or hyper-flexion.

In another embodiment, the device can be used to create prosthetic limbs. Specifically, the flexural member can lengthen to adjust for a growing limb or to make slight adjustment in order to match the size of a homologous limb.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A distractible intervertebral body fusion device for implantation into an intervertebral disc space in a patient's body, comprising:
a top end plate having a top bearing surface configured to interface with an end plate of a superior vertebra of the intervertebral disc space;
a bottom end plate having a bottom bearing surface configured to interface with an end plate of an inferior vertebra of the intervertebral disc space; and
at least two struts connecting the top end plate and the bottom end plate, each strut comprising first and second structural members and a block, wherein each structural member is connected at one end to one of the end plates with a flexure member and at an opposed end to the block with a flexure member, and wherein the blocks include apertures enabling operable access to an expansion tool such that actuation of the expansion tool in a first direction drives the blocks closer together, causing the struts to expand, thereby distracting the top end plate and the bottom end plate with respect to each other,
wherein one of the end plates provides a backstop for each flexure connecting one of the structural members with the respective end plate, the backstop providing a rolling contact with the flexure that guides a curvature of the flexure as the top and bottom end plates distract, the curvature of the flexure conforming to a shape of the backstop, and wherein the backstops are one of concave or convex.

2. The device of claim 1, wherein the top end plate, bottom end plate and at least two struts comprise a one piece unitary body.

3. The device of claim 1, wherein there are at least two struts on a first side of the device and at least two struts on an opposing side of the device.

4. The device of claim 1, wherein the flexure members are selected from the group consisting of: band flexures, circular flexures, elliptical flexures, and leaf flexures.

5. The device of claim 1, wherein the top end plate, bottom end plate and at least two struts comprise a ductile material.

6. The device of claim 1, wherein the top end plate and bottom end plate each have an opening defined therein configured to allow bone growth into an open space defined by the device.

7. The device of claim 1, wherein the top bearing surface and bottom bearing surface each have a plurality of teeth extending outwardly therefrom.

8. The device of claim 1, wherein as the device is distracted from a compressed configuration to a distracted configuration, an ever increasing portion of each flexure conforms to the shape of the respective backstop.

9. The device of claim 1, wherein each end plate provides at least a pair of backstops, the pair of backstops being continuous and symmetrical with each other, each backstop providing a rolling contact for a different flexure.

10. A distractible intervertebral body fusion device for implantation into an intervertebral disc space in a patient's body, comprising:
a top end plate having a top bearing surface configured to interface with an end plate of a superior vertebra of the intervertebral disc space;
a bottom end plate having a bottom bearing surface configured to interface with an end plate of an inferior vertebra of the intervertebral disc space; and
at least two struts connecting the top end plate and the bottom end plate, each strut comprising first and second structural members and a block, wherein each structural member is connected at one end to one of the end plates with a flexure member and at an opposed end to the block with a flexure member, and wherein the blocks include apertures enabling operable access to an expansion tool such that actuation of the expansion tool in a first direction drives the blocks closer together, causing the struts to expand, thereby distracting the top end plate and the bottom end plate with respect to each other,
wherein one of the end plates provides a backstop for each flexure connecting one of the structural members with the respective end plate, the backstop providing a rolling contact with the flexure that guides a curvature of the flexure as the top and bottom end plates distract, the curvature of the flexure conforming to a shape of the backstop, and wherein there are three struts on the first side and three struts on the opposing side.

11. The device of claim 10, wherein the backstops are flat.

12. The device of claim 10, wherein as the device is distracted from a compressed configuration to a distracted configuration, an ever increasing portion of each flexure conforms to the shape of the respective backstop.

13. The device of claim 10, wherein each end plate provides at least a pair of backstops, the pair of backstops being continuous and symmetrical with each other, each backstop providing a rolling contact for a different flexure.

14. A medical device capable of being distracted from a collapsed configuration to an expanded configuration, comprising:
- a top end plate;
- a bottom end plate; and
- at least two struts connecting the top end plate and the bottom end plate, each strut comprising first and second structural members and a block, wherein each structural member is connected at one end to one of the end plates with a flexure member and at an opposed end to the block with a flexure member, and wherein the blocks include apertures enabling operable access to an expansion tool such that actuation of the expansion tool in a first direction drives the blocks closer together, causing the struts to expand, thereby distracting the top end plate and the bottom end plate with respect to each other, wherein one of the end plates provides a backstop for each flexure connecting one of the structural members with the respective end plate, the backstop configured to provide a rolling contact with the flexure and guide a curvature of the flexure as the top and bottom end plates distract, the curvature of the flexure conforming to a shape of the backstop, wherein the backstops are one of concave or convex.

15. The device of claim 14, wherein the top end plate, bottom end plate and at least two struts comprise a one piece unitary body.

16. The device of claim 14, wherein as the device is distracted from a compressed configuration to a distracted configuration, an ever increasing portion of each flexure conforms to the shape of the respective backstop.

17. The device of claim 14, wherein each end plate provides at least a pair of backstops, the pair of backstops being continuous and symmetrical with each other, each backstop providing a rolling contact for a different flexure.

* * * * *

UNITED STATES PATENT AND TRADEMARK OFFICE
CERTIFICATE OF CORRECTION

PATENT NO. : 8,523,944 B2  
APPLICATION NO. : 12/650994  
DATED : September 3, 2013  
INVENTOR(S) : Jimenez et al.

Page 1 of 1

It is certified that error appears in the above-identified patent and that said Letters Patent is hereby corrected as shown below:

On the title page under Item "(60) Related U.S. Application Data" please insert the following:

Item --(63) Continuation of application No. PCT/US2009/069876, filed on December 30, 2009.--

Signed and Sealed this
Eleventh Day of February, 2014

Michelle K. Lee
*Deputy Director of the United States Patent and Trademark Office*